(12) United States Patent
Maimon

(10) Patent No.: US 10,172,904 B2
(45) Date of Patent: Jan. 8, 2019

(54) HERBAL FORMULATIONS

(71) Applicant: Yair N. Maimon, Ramat Gan (IL)

(72) Inventor: Yair N. Maimon, Ramat Gan (IL)

(73) Assignee: LIFEBIOTIC MEDICAL RESEARCH LTD, Tel-Aviv (IL)

( * ) Notice: Subject to any disclaimer, the term of this patent is extended or adjusted under 35 U.S.C. 154(b) by 0 days.

(21) Appl. No.: 15/170,412

(22) Filed: Jun. 1, 2016

(65) Prior Publication Data

US 2016/0303180 A1  Oct. 20, 2016

Related U.S. Application Data

(63) Continuation of application No. 14/043,969, filed on Oct. 2, 2013, now Pat. No. 9,370,543, which is a continuation of application No. 13/120,877, filed as application No. PCT/IL2009/000923 on Sep. 24, 2009, now Pat. No. 8,574,636.

(60) Provisional application No. 61/136,696, filed on Sep. 25, 2009.

(51) Int. Cl.

| A61K 36/00 | (2006.01) |
|---|---|
| A61K 36/8968 | (2006.01) |
| A61K 36/23 | (2006.01) |
| A61K 36/258 | (2006.01) |
| A61K 36/284 | (2006.01) |
| A61K 36/481 | (2006.01) |
| A61K 36/536 | (2006.01) |
| A61K 36/539 | (2006.01) |
| A61K 36/638 | (2006.01) |
| A61K 36/65 | (2006.01) |
| A61K 36/748 | (2006.01) |
| A61K 36/752 | (2006.01) |
| A61K 36/815 | (2006.01) |
| A61K 9/00 | (2006.01) |
| A61K 9/20 | (2006.01) |
| A61K 9/48 | (2006.01) |
| A61K 31/337 | (2006.01) |
| A61K 31/513 | (2006.01) |
| A61K 31/664 | (2006.01) |
| A61K 31/704 | (2006.01) |
| A61K 36/076 | (2006.01) |
| A61K 36/486 | (2006.01) |
| A61K 45/06 | (2006.01) |

(52) U.S. Cl.

CPC ........ *A61K 36/8968* (2013.01); *A61K 9/0053* (2013.01); *A61K 9/20* (2013.01); *A61K 9/48* (2013.01); *A61K 31/337* (2013.01); *A61K 31/513* (2013.01); *A61K 31/664* (2013.01); *A61K 31/704* (2013.01); *A61K 36/00* (2013.01); *A61K 36/076* (2013.01); *A61K 36/23* (2013.01); *A61K 36/258* (2013.01); *A61K 36/284* (2013.01); *A61K 36/481* (2013.01); *A61K 36/486* (2013.01); *A61K 36/536* (2013.01); *A61K 36/539* (2013.01); *A61K 36/638* (2013.01); *A61K 36/65* (2013.01); *A61K 36/748* (2013.01); *A61K 36/752* (2013.01); *A61K 36/815* (2013.01); *A61K 45/06* (2013.01)

(58) Field of Classification Search

CPC .................................................... A61K 36/00
See application file for complete search history.

(56) References Cited

U.S. PATENT DOCUMENTS

| 6,340,482 B1 | 1/2002 | Jones |
| 2002/0098249 A1 | 7/2002 | No |
| 2003/0211180 A1 | 11/2003 | Cheng et al. |
| 2004/0109904 A1 | 6/2004 | Li |
| 2004/0219226 A1* | 11/2004 | Lee ........................ A61K 36/11 424/541 |

FOREIGN PATENT DOCUMENTS

| CN | 1083714 A | * | 3/1994 | |
| CN | 1096957 A | * | 1/1995 | |
| CN | 1135904 A | | 11/1996 | |
| CN | 1265901 A | * | 9/2000 | |
| CN | 1449812 A | * | 10/2003 | ............. A61K 36/11 |
| CN | 101066125 A | | 11/2007 | |
| CN | 101152382 A | | 4/2008 | |
| CN | 101269187 A | * | 9/2008 | |
| WO | 02/02607 A2 | | 1/2002 | |

OTHER PUBLICATIONS

Bai et al, Clinical study on the application of integrated traditional and western medicine in treating chronic renal failure. Chinese Journal of Information on Traditional Chinese Medicine (2005), vol. 12, No. 9, pp. 14-15.*
Bensky, et al., Chinese Herbal Medicine: Materia Medica, 3rd edition, (2004).
Campbell, et al., "Antiproliferative Activity of Chinese Medicinal Herbs on Breast Cancer Cells In Vitro", Anticancer Research, vol. 22, pp. 3843-3852, (2002).
Liu, et al., "Effects of Sheng-Mai Injection on the PRPP synthetase activity in BFU-Es and CFU-Es from bone marrows of mice with benzene-induced aplastic anemie"; LifeSciences, vol. 69, No. 12, pp. 1371-1379, (2001). XP-002574796, Database accession No. PREV200100436221, abstract.
LV, et al., "Study on effect of Astragalus membranaceus injection on hematopoiesis in anemic mice with myelosuppression", Zhong Yao Cai, vol. 28, No. 9, pp. 791-793, (2005). XP-002574794, Database accession No. NLM16447871, abstract.

(Continued)

*Primary Examiner* — Qiuwen Mi
(74) *Attorney, Agent, or Firm* — Vorys, Sater, Seymour & Pease LLP

(57) ABSTRACT

A formulation comprising a variety of Chinese herbs is disclosed for the treatment of cancer and side effects associated with the treatment of cancer.

3 Claims, 5 Drawing Sheets

(56) References Cited

OTHER PUBLICATIONS

Pan, et al., "Effect of Fuzheng Yiliu decoction combined with chemotherapy on patients with intermediate and late stage gastrointestinal cancer", World Journal of Gastroenterology, vol. 11, No. 3, pp. 439-442, (2005).

Shen, et al., "Antioxidant and antiplatelet effects of Dang-Gui-Shao-Yao-San on human blood cells", American Journal of Chinese Medicine, vol. 33, No. 5, pp. 747-758, (2005). XP-002574795, Database accession No. PREV200510244066, abstract.

Yaal-Hahoshen, et al., "A Prospective, Controlled Study of the Botanical Compound Mixture LCS101 for Chemotherapy-Induced Hematological Complications in Breast Cancer", The Oncologist, vol. 16, No. 9, pp. 1197-1202, (2001).

Skin disorder from Merck Manual, pp. 1-2, Accessed Feb. 3, 2009.

Vitiligo from Merck Manual, pp. 1-2, Accessed Feb. 3, 2009.

Walker, Personality, coping and sex as psychosocial aspects of psoriatic arthropathy, Dermatology and Psychosomatics, (2003), vol. 4, No. 1, pp. 27-32.

Yu et al., Effects of long-term oral administration of polymeric microcapsules containing tyrosinase on maintaining decreased systemic tyrosine levels in rats, Journal of pharmaceutical sciences, (Apr. 2004), vol. 93, No. 4, pp. 831-837.

Cleaver, Defective repair replication of DNA in xeroderma pigmentosum, Nature [London], (1968), vol. 218, No. 5142, pp. 652-656.

Granger et al., Association between dietary fat and skin cancer in an Australian population using case-control and cohort study designs, BMC Cancer (2006), vol. 6, pp. 1-7.

\* cited by examiner

Control     Formulation (3 mg/ml)     Formulation (50 mg/ml)

HERBAL FORMULATIONS

FIELD OF THE INVENTION

This invention generally relates to herbal formulations and uses thereof in improving the well being of a subject, and which may additionally be used in e.g., adjuvant therapy for patients suffering from a variety of disorders, e.g., cancer.

BACKGROUND OF THE INVENTION

Medicinal herbs have been traditionally used for a variety of purposes, particularly to prevent and treat a variety of diseases including cancer. Some of the most important chemotherapeutic agents used in the treatment of breast cancer are derivatives of herbal remedies. These include the taxanes obtained from the Pacific yew tree, Taxus brevifolia reserpine, and vincristine and vinblastine which are obtained from the Rosy periwinkle shrub. The use of botanical medicine is widespread in all regions of the developing world and is rapidly growing in industrialized countries especially among patients diagnosed with life-threatening diseases such as cancer.

Despite their broad use, there exists insufficient scientific data on the safety and efficacy of many of the herbal therapies. Recently, a large in vitro study on the effect of more than 70 Chinese herbs extracts on growth of five breast cancer cell lines found that 21% of the herbal extracts demonstrated more than 50% growth inhibition on at least 4 from the 5 cell lines [1].

The emphasis of the Chinese medicine is on the treatment of the body as a whole. Chinese medicine views include a three-fold approach of using herbs that treat (I) the vitality (tonifying herbs), (II) the cancer (anti-cancer herbs) and (III) the side effects of chemotherapy.

In the Materia Medica of Chinese medicine [2], these herbs are selected from 8 classic categories (which are used traditionally to categorize Chinese herbs): (1) herbs that tonify the Qi; (2) herbs that tonify Blood; (3) herbs that clear heat and relieve toxicity; (4) herbs that clear heat and fire; (5) herbs that regulate the flow of Qi; (6) herbs that drain "dampness"; (7) herbs that invigorate the blood; and (8) herbs that tonify the Yin.

REFERENCES

[1] Campbell M J, Hamilton B, Shoemaker M, Tagliaferri M, Cohen I, Tripathy D Antiproliferative activity of Chinese medicinal herbs on breast cancer cells in vitro Anticancer Res. 2002 November-December; 22(6C): 3843-52.

[2] Bensky Dan and Gamble Andrew Chinese Herbal Medicine: Materia Medica Eastland press, Seattle, Wash. 98111, USA.

SUMMARY OF THE INVENTION

The inventors of the present invention have now designed and successfully practiced unique formulations comprising a combination of herbs. The formulations were tested in vitro as well as in vivo on human subjects and were found to substantially improve the well-being of a subject suffering from a life-threatening disease or disorder or from a condition which is associated therewith. In particular, the formulations of the invention have been found effective in ameliorating multiple side effects associated with chemotherapy and in imposing anti-proliferative effect on the cancer cells.

Thus, in one aspect of the present invention there is provided a herbal formulation comprising a combination of at least four herbs, each being selected from:
  at least one herb that tonifies the Qi;
  at least one herb that drains dampness;
  at least one herb that tonifies blood;
  at least one herb that invigorates the blood;
  at least one herb that regulates the flow of Qi;
  at least one herb that tonifies yin;
  at least one herb that clears heat and relieves toxicity; and
  at least one herb that clears heat and fire.

Each herb may be in a solid or liquid form or in a solution form, namely dissolved in a solid or liquid carrier.

For purposes of clarity, it should be noted that a formulation according to the invention comprises at least 4 herbs, each being selected from a different category of the categories listed above. The formulation may comprise more than 4 herbs; however, at least 4 of which are of different categories. For example, one formulation according to the invention may comprise one herb that tonifies the Qi, one herb that drains dampness, one herb that tonifies blood and one herb that invigorates the blood. A second formulation may comprise a combination of 5 herbs as follows: two herbs that tonify the Qi, one herb that drains dampness, one herb that tonifies blood and one herb that invigorates the blood. A different formulation comprising a combination of 5 herbs may comprise one herb that tonifies the Qi, one herb that drains dampness, one herb that tonifies blood, one herb that clears heat and fire and one herb that invigorates the blood. Thus, any such combination is within the scope of the present invention, even if not mentioned per se.

Additionally, it should be noted that in the specification provided below, for each herbal component of a formulation of the invention, two names are provided for each herb: a Latin name and a Chinese name. In the terminology used herein, the Latin name is given first, followed by the Chinese name which is typically given in parenthesis. For example, for the herb referred to as "Astragalus Membranaceus (Huang Qi)", Astragalus Membranaceus is the Latin name and Huang Qi is its Chinese name.

As used herein the term "tonifies the Qi" refers to a herb (or a herbal component) that strengthens the vitality and enhances the immune system and that has a general tonic effect and strengthening weakness. The at least one herb that tonifies the Qi is thus selected from Astragalus Membranaceus (Huang Qi), Atractylodes Macrocephala (Bai zhu), Ginseng Radix (Ren Shen), Radix Codonopsitis Pilosulae (Dang Shen), Pseudostellaiae Heterophillae (Tai Zi Shen) and Redix Glycyrrhizae Uralensis (Gan Cao).

The term "drains dampness" refers to a herb (or a herbal component) of the formulation which effects the fluid production in the body, in particular the pathogenic formation of fluids such as phlegm, edema, and any fluid associated swelling. The term also refers to a herb which has a diuretic effect. The at least one herb that drains dampness is selected from Poriae Cocos (Fu Ling), Coicis Lachryma-jobi Semen (Yi Yi Ren), Herba Lobeliae Chinensis Cum Radice (Ban Bian Lian), Semen Plantaginis (Che Qian Zi), Fructus Kochia Scopariae (Di Fu Zi) and Rhizoma Alismatis (Ze Xie).

The term "tonifies blood" refers to a herb (or a herbal component) which enhances the formation of blood. The at least one herb that tonifies blood is selected from Lycium Chinense (Gou Qi Zi), Radix Paeoniae Lactiflorae (Bai Shao), Radix Angelica Sinensis (Dang Gui), Arilus Euphoriae Longanae (Long Yang Rao), Mori Albae Fructus (Sang Shen), Rhemanniae Glutinosae Conquitae Radix (Shu Di Huang) and Radix Polygonum multiflorum (He Shou wu).

The term "invigorates the blood" refers to a herb (or a herbal component) which effects movement, fluidity and/or coagulation of blood. The at least one herb that invigorates the blood is selected from Paeonia Obovata (Chi Shao), Radix Salviae Miltiorrhizae (Dan Shen), Radix Ligustici Chuanxiong (Chuanxiong), Flos Carthami Tinctorii (Homg Hua), Radix Et Caulis Jixueteng (Ji Xue Tang), Curcumae, Tuber (Yu Jin), Persicae, Semen (Tao Ren) and Curcuma Zedoaria (E-Zhu).

The term "regulates the flow of Qi" refers to a herb (or a herbal component) which regulates the malfunction and obstruction and, in particular, gastrointestinal dysfunction which causes pain or malabsorption. The at least one herb that regulates the flow of Qi is selected from Citrus Reticulata (Chen Pi), Aucklandiae Lappae Radix (Mu Xiang), Diospyri Kaki Calyx (Xi Di), Cyperi Rotundi Rhizoma (Xiang Fu), Citri Aurantii Fructus (Zhi Ke) and Citri Aurantii Fructus Immaturus (Zhi Shi).

The term "tonifies yin" refers to a herb (or a herbal component) which enhances bodily function by strengthening, nourishing and moistening, i.e., by providing the nourishment required for cellular growth and by increasing the production of physiological fluids when there is dryness. The at least one herb that tonifies the yin is selected from Ligustrum Lucidum (Niu Zhen Zhi), Ophiopogon Japonicus (Mai men Dong), Glehnia Littoralis (Bei Sha Shen), Sangjisheng, Ramulus (Sang Zi Sheng), Plastrum, Testudinis (Gui Ban), Ophiopogonis Japonici, Tuber (Maimen Dong), Panacis Quinquefolii, Radix (Xi Yang Shen) and Radix Adenophorae Seu Glehniae (Sha Shen).

The term "clears heat and relieves toxicity" refers to a herb (or a herbal component) which treats fever and infections including purulent infections and abscesses and which has at least one of the effects selected from an antiviral effect, an antibacterial effect, an anti-inflammatory effect and anti-infectious effect. The at least one herb that clears heat and relieves toxicity is selected from Oldenlandia Diffusa (Bai Hua She She cao), Scutellaria Barbata (Ban Zhi Lian), Radix Isatidis Seu Baphicacanthi (Ban Lan Gen), Flos Lonicerae Japonicae (Jin Yin Hua), Taraxaci Mongolici Cum Radice Herba (Pu Gong Yin), Sophorae Subprostratae Radix (Shan Dou Gen), Smilacis Glabrae, Rhizoma (Tu Fu Ling) and Pseudobulbus Shancigu (Shan Ci Gu).

The term "clears heat and fire" refers to a herb (or a herbal component) which treats high fever and side effects thereof such as irritability, thirst, delirium or any other side effect associated with high fever as known in the art. The at least one herb that clears heat and fire is selected from Prunella Vulgaris (Xia Ku Cao), Rhizoma, Phragmitis Communis (Lu Gen), Gardeniae Jasminoidis Fructus (Zhi Zi), Anemarrhenae Asphodeloidis Rhizoma (Zi Mu), Nelumbinis Nuciferae Semen (Lian Xin) and Herba Lophatheri Gracilis (Dan Zhu Ye).

In some embodiments, the herbal formulation comprises a combination of herbs, at least one herb of each of said categories.

In some embodiments, the herbal formulation comprises at least one herb that tonifies the Qi, at least one herb that tonifies blood, at least one herb that clears heat and fire and at least one herb that clears heat and relieves toxicity.

In some other embodiments, the herbal formulation comprises two herbs that tonify the Qi, three herbs that tonify blood, three herbs that tonify yin, two herbs that clear heat and relieve toxicity, one herb that clears heat and fire, one herb that regulates the flow of Qi, one herb that drains dampness and one herb that invigorates the blood.

In some embodiments, the herbs that tonify the Qi are Astragalus Membranaceus (Huang Qi) and/or Atractylodes Macrocephala (Bai zhu); the herbs that tonify blood are Lycium Chinense (Gou Qi Zi) and/or Paeonia Lactiflora (Bai Shao) and/or Milletia Reticulata (Ji Xue Teng); the herbs that tonify yin are Ligustrum Lucidum (Niu Zhen Zhi) and/or Ophiopogon Japonicus (Mai men Dong) and/or Glehnia Littoralis (Bei Sha Shen); the herbs that clear heat and relieve toxicity are Oldenlandia Diffusa (Bai Hua She She cao) and/or Scutellaria Barbata (Ban Zhi Lian); the herb that clears heat and fire may be Prunella Vulgaris (Xia Ku Cao); the herb that regulates the flow of Qi may be Citrus Reticulata (Chen Pi); the herb that drains dampness may be Poriae Cocos (Fu Ling); and the herb that invigorates the blood may be Paeonia Obovata (Chi Shao).

In further embodiments, the herbs that tonify the Qi are Astragalus Membranaceus (Huang Qi) and Atractylodes Macrocephala (Bai zhu); the herbs that tonify blood are Lycium Chinense (Gou Qi Zi), Paeonia Lactiflora (Bai Shao) and Milletia Reticulata (Ji Xue Teng); the herbs that tonify yin are Ligustrum Lucidum (Niu Zhen Zhi), Ophiopogon Japonicus (Mai men Dong) and Glehnia Littoralis (Bei Sha Shen); the herbs that clear heat and relieve toxicity are Oldenlandia Diffusa (Bai Hua She She cao) and Scutellaria Barbata (Ban Zhi Lian); the herb that clears heat and fire is Prunella Vulgaris (Xia Ku Cao); the herb that regulates the flow of Qi is Citrus Reticulata (Chen Pi); the herb that drains dampness is Poriae Cocos (Fu Ling); and the herb that invigorates the blood is Paeonia Obovata (Chi Shao).

In further embodiments, a formulation according to the invention comprises Astragalus Membranaceus (Huang Qi), Poriae Cocos (Fu Ling), Atractylodes Macrocephala (Bai zhu), Lycium Chinense (Gou Qi Zi), Ligustrum Lucidum (Niu Zhen Zhi), Paeonia Lactiflora (Bai Shao), Paeonia Obovata (Chi Shao), Citrus Reticulata (Chen Pi), Ophiopogon Japonicus (Mai men Dong), Milletia Reticulata (Ji Xue Teng), Oldenlandia Diffusa (Bai Hua She She cao), Scutellaria Barbata (Ban Zhi Lian), Prunella Vulgaris (Xia Ku Cao) and Glehnia Littoralis (Bei Sha Shen).

In some embodiments, the formulation comprises between about 1-30% Astragalus Membranaceus (Huang Qi), between about 1-20% Poriae Cocos (Fu Ling), between about 1-20% Atractylodes Macrocephala (Bai zhu), between about 1-30% Lycium Chinense (Gou Qi Zi), between about 1-30% Ligustrum Lucidum (Niu Zhen Zhi), between about 1-30% Paeonia Lactiflora (Bai Shao), between about 1-20% Paeonia Obovata (Chi Shao), between about 1-20% Citrus Reticulata (Chen Pi), between about 1-30% Ophiopogon Japonicus (Mai men Dong), between about 1-30% Milletia Reticulata (Ji Xue Teng), between about 1-45% Oldenlandia Diffusa (Bai Hua She She cao), between about 1-45% Scutellaria Barbata (Ban Zhi Lian), between about 1-45% Prunella Vulgaris (Xia Ku Cao) and between about 1-30% Glehnia Littoralis (Bei Sha Shen).

In further embodiments, the formulation comprises between about 5-20% Astragalus Membranaceus (Huang Qi), between about 2-10% Poriae Cocos (Fu Ling), between about 2-10% Atractylodes Macrocephala (Bai zhu), between about 3-15% Lycium Chinense (Gou Qi Zi), between about 5-30% Ligustrum Lucidum (Niu Zhen Zhi), between about 4-30% Paeonia Lactiflora (Bai Shao), between about 2-19% Paeonia Obovata (Chi Shao), between about 1-10% Citrus Reticulata (Chen Pi), between about 2-10% Ophiopogon Japonicus (Mai men Dong), between about 5-12% Milletia Reticulata (Ji Xue Teng), between about 7-45% Oldenlandia Diffusa (Bai Hua She She cao), between about 5-28% Scutellaria Barbata (Ban Zhi Lian), between about 5-35% Prunella Vulgaris (Xia Ku Cao) and between about 5-20% Glehnia Littoralis (Bei Sha Shen).

In further embodiments, the formulation comprises between about 5-10% Astragalus Membranaceus (Huang Qi), between about 2-10% Poriae Cocos (Fu Ling), between about 3-10% Atractylodes Macrocephala (Bai zhu), between about 5-10% Lycium Chinense (Gou Qi Zi), between about 5-15% Ligustrum Lucidum (Niu Zhen Zhi), between about 4-12% Paeonia Lactiflora (Bai Shao), between about 2-10% Paeonia Obovata (CM Shao), between about 1-8% Citrus Reticulata (Chen Pi), between about 2-8% Ophiopogon Japonicus (Mai men Dong), between about 5-10% Milletia Reticulata (Ji Xue Teng), between about 7-20% Oldenlandia Diffusa (Bai Hua She She cao), between about 5-15% Scutellaria Barbata (Ban Zhi Lian), between about 5-15% Prunella Vulgaris (Xia Ku Cao) and between about 5-15% Glehnia Littoralis (Bei Sha Shen).

In some embodiments, the formulation comprises about 8.1% Astragalus Membranaceus (Huang Qi), about 4.9% Poriae Cocos (Fu Ling), about 4.9% Atractylodes Macrocephala (Bai zhu), about 6.5% Lycium Chinense (Gou Qi Zi), about 8.1% Ligustrum Lucidum (Niu Zhen Zhi), about 6.5% Paeonia Lactiflora (Bai Shao), about 4.9% Paeonia Obovata (Chi Shao), about 4.9% Citrus Reticulata (Chen Pi), about 6.5% Ophiopogon Japonicus (Mai men Dong), about 8.1% Milletia Reticulata (Ji Xue Teng), about 12.2% Oldenlandia Diffusa (Bai Hua She She cao), about 9.8% Scutellaria Barbata (Ban Zhi Lian), about 8.1% Prunella Vulgaris (Xia Ku Cao) and about 6.5% Glehnia Littoralis (Bei Sha Shen).

In some embodiments, the herbal formulation further comprises at least one further herb selected from Cordyceps Sinensis (dong chong xia cao), Schizandra Chinensis (Wu Wei Zi), Commiphora Molmol (Mo Yao), Anemarrhena asphodeloides (Zhi mu), Pseudostellariae Heterophyllae (Tai Zhi Shen), Radix Glycyrrhizae (Gan Cao), Massa Fermentata (Shen Qu), Fructus Hordei Germinatus (Mai Ya) and Gigeriae galli Endothelium corneum (Ji Nei Jin).

In further embodiments, the at least one further herb is added in an amount ranging between about 1 and 30% of the total weight of the herbal formulation. In some embodiments, Cordyceps Sinensis (Dong Chong Xia Cao) may be present in the formulation in an amount between about 1 and 30%, Schizandra Chinensis (Wu Wei Zi) in an amount between about 1 and 20%, Commiphora Molmol (Mo Yao) in an amount between about 1 and 20%, Anemarrhena asphodeloides (Zhi Mu) in an amount between about 1 and 20%, Pseudostellariae Heterophyllae (Tai Zhi Shen) in an amount between 1 and 30%, Radix Glycyrrhizae (Gan Cao) in an amount between about 1 and 20%, Massa Fermentata (Shen Qu) in an amount between about 1 and 20%, Fructus Hordei Germinatus (Mai Ya) in an amount between about 1 and 10% and Gigeriae galli Endothelium corneum (Ji Nei Jin) in an amount between 1 and 10% of the total weight (wt %) of the formulation.

In some embodiments, the formulation may further comprise at least one additional herb that tonifies the Qi, said herb being selected from Ginseng Radix (Ren Shen), Rhizoma Atractylodis Macrocephalae (Bai Zhu), Radix Codonopsitis Pilosulae (Dang Shen), Ganoderma Lucidum (Reishi), Pseudostellaiae Heterophillae Radix (Tai Zi Shen) and Redix Glycyrrhizae Uralensis (Gan Cao).

In some embodiments, the at least one additional herb that tonifies the Qi is present in the formulation in the following amounts: about 1-30% Ginseng Radix (Ren Shen), about 1-30% Rhizoma Atractylodis Macrocephalae (Bai Zhu), about 1-30% Radix Codonopsitis Pilosulae (Dang Shen), about 1-20% Ganoderma Lucidum (Reishi), about 1-20% Pseudostellaiae Heterophillae Radix (Tai Zi Shen) and about 1-20% Redix Glycyrrhizae Uralensis (Gan Cao).

In some embodiments, the formulation further comprises at least one herb that drains dampness, said herb being selected from Coicis Lachryma-jobi Semen (Yi Yi Ren), Herba Lobeliae Chinensis Cum Radice (Ban Bian Lian), Semen Plantaginis (Che Qian Zi), Fructus Kochia Scopariae (Di Fu Zi) and Alismatis Orientalis, Rhizoma (Ze Xie).

In some embodiments, the at least one additional herb that drains dampness is present in the formulation in the following amounts: about 1-30% Coicis Lachryma-jobi Semen (Yi Yi Ren), about 1-20% Herba Lobeliae Chinensis Cum Radice (Ban Bian Lian), about 1-20% Semen Plantaginis (Che Qian Zi), about 1-20% Fructus Kochia Scopariae (Di Fu Zi) and about 1-20% Alismatis Orientalis, Rhizoma (Ze Xie).

In some embodiments, the formulation further comprises at least one additional herb that tonifies blood, said herb being selected from Radix Paeoniae Lactiflorae (Bai Shao), Radix Angelica Sinensis (Dang Gui), Arilus Euphoriae Longanae (Long Yang Rao), Mori Albae Fructus (Sang Shen) and Rhemanniae Glutinosae Conquitae Radix (Shu Di Huang).

In some embodiments, the at least one herb that tonifies blood is present in the formulation in the following amounts: about 1-30% Radix Paeoniae Lactiflorae (Bai Shao), about 1-30% Radix Angelica Sinensis (Dang Gui), about 1-30% Arilus Euphoriae Longanae (Long Yang Rao), about 1-30% Mori Albae Fructus (Sang Shen) and about 1-30% Rhemanniae Glutinosae Conquitae Radix (Shu Di Huang).

In some embodiments, the formulation further comprises at least one additional herb that tonifies the yin, said herb being selected from Sangjisheng, Ramulus (Sang Zi Sheng), Plastrum, Testudinis (Gui Ban), Ophiopogonis Japonici, Tuber (Mai Men Dong), Panacis Quinquefolii, Radix (Xi Yang Shen) and Adenophorae Seu Glehniae and Radix (Sha Shen).

In some embodiments, the at least one additional herb that tonifies the yin is present in the formulation in the following amounts: about 1-30% Sangjisheng, Ramulus (Sang Zi Sheng), about 1-30% Plastrum Testudinis (Gui Ban), about 1-30% Ophiopogonis Japonici Tuber (Mai Men Dong), about 1-30% Panacis Quinquefolii Radix (Xi Yang Shen) and about 1-30% Adenophorae Seu Glehniae Radix (Sha Shen).

In some embodiments, the formulation further comprises at least one additional herb that invigorates blood, said herb being selected from Radix Salviae Miltiorrhizae (Dan Shen), Radix Ligustici Chuanxiong, Flos Carthami Tinctorii (Homg Hua), Radix Et Caulis Jixueteng (Ji Xue Tang), Curcumae Tuber (Yu Jin), Persicae Semen (Tao Ren) and Curcuma Zedoaria (E-Zhu).

In some embodiments, the at least one additional herb that invigorates blood is present in the formulation in the following amounts: about 1-30% Radix Salviae Miltiorrhizae (Dan Shen), about 1-30% Radix Ligustici Chuanxiong (Chuanxiong), about 1-30% Flos Carthami Tinctorii (Homg Hua), about 1-30% Radix Et Caulis Jixueteng (Ji Xue Tang), about 1-30% Curcumae Tuber (Yu Jin), about 1-30% Persicae Semen (Tao Ren) and about 1-30% Curcuma Zedoaria (E-Zhu).

In some embodiments, the formulation further comprises at least one additional herb that regulates the flow of Qi, said herb being selected from Aucklandiae Lappae Radix (Mu Xiang), Diospyri Kaki Calyx (Shi Di), Cyperi Rotundi Rhizoma (Xiang Fu), Citri Aurantii Fructus (Zhi Ke) and Citri Aurantii Fructus Immaturus (Zhi Shi).

In some embodiments, the at least one additional herb that regulates the flow of Qi is present in the formulation in the following amounts: about 1-20% Aucklandiae Lappae Radix (Mu Xiang), about 1-20% Diospyri Kaki Calyx (Shi DI), about 1-20% Cyperi Rotundi Rhizoma (Xiang Fu), about 1-20% Citri Aurantii Fructus (Zhi Ke) and about 1-20% Citri Aurantii Fructus Immaturus (Zhi Shi).

In some embodiments, the formulation further comprises at least one additional herb that clears heat and relieves toxicity, said herb being selected from Radix Isatidis Seu Baphicacanthi (Ban Lan Gen), Herba Scutellariae Barbatae (Ban Zhi Lian), Flos Lonicerae Japonicae (Jin Yin Hua), Taraxaci Mongolici Cum Radice Herba (Pu Gong Yin), Sophorae Subprostratae Radix (Shan Dou Gen), Smilacis Glabrae, Rhizoma (Tu Fu Ling) and Pseudobulbus Shancigu (Shan Ci Gu).

In some embodiments, the at least one herb that clears heat and relieves toxicity is present in the formulation in the following amounts: about 1-45% of Radix Isatidis Seu Baphicacanthi (Ban Lan Gen), about 1-45% Herba Scutellariae Barbatae (Ban Zhi Lian), about 1-45% Flos Lonicerae Japonicae (Jin Yin Hua), about 1-45% Taraxaci Mongolici Cum Radice Herba (Pu Gong Yin), about 1-45% Sophorae Subprostratae Radix (Shan Dou Gen), about 1-45% Smilacis Glabrae, Rhizoma (Tu Fu Ling) and about 1-45% Pseudobulbus Shancigu (Shan Ci Gu).

In some embodiments, the formulation further comprises at least one additional herb that clears heat and fire, said herb being selected from Rhizoma, Phragmitis Communis (Lu Gen), Gardeniae Jasminoidis Fructus (Zhi Zi), Anemarrhenae Asphodeloidis Rhizoma (Zi Mu), Nelumbinis Nuciferae Semen (Lian Xin) and Herba Lophatheri Gracilis (Dan Zhu Ye).

In some embodiments, the at least one herb that clears heat and fire is present in the formulation in the following amounts: about 1-30% Rhizoma, Phragmitis Communis (Lu Gen), about 1-30% Gardeniae Jasminoidis Fructus (Zhi Zi), about 1-30% Anemarrhenae Asphodeloidis Rhizoma (Zi Mu), about 1-30% Nelumbinis Nuciferae Semen (Lian Xin) and about 1-30% Herba Lophatheri Gracilis (Dan Zhu Ye).

In some further embodiments, the formulation further comprises at least one astringent herb selected from Corni Officinalis Fructus (Shan Zhu Yu), Semen Nelumbinis Nuciferae (Lian Zi), Pruni Mume Fructus (Wu Mai), Myristicae Fragrantis Semen (Rou Dou Kou), Fructus Terminaliae Chebulae (He Zi) and Schizandra Chinensis (Wu Wei Zi).

In such embodiments, the at least one astringent herb is present in the formulation in the following amounts: about 1-30% Corni Officinalis Fructus (Shan Zhu Yu), about 1-30% Semen Nelumbinis Nuciferae (Lian Zi), about 1-30% Pruni Mume Fructus (Wu Mai), about 1-30% Myristicae Fragrantis Semen (Rou Dou Kou), about 1-30% Fructus, Terminaliae Chebulae (He Zi) and about 1-30% Schizandra Chinensis (Wu Wei Zi).

In some further embodiments, the formulation of the invention comprises or consists the combination of herbs listed in any of Tables 1 to 9, the combination being in the wt % indicated or at any other wt %.

In further embodiments, the formulation of the invention is any formulation comprising a combination of at least 4 herbs listed in any one of Tables 1 to 9. In further embodiments, the formulation of the invention comprises the combination of herbs depicted in any one of Tables 1 to 9.

The herbal components of the formulations of the invention may be obtained by any one method known in the art. The formulations of the invention are typically prepared by mixing (admixing) the herbal components together in the presence or absence of a carrier, an excipient or a diluent.

The herbal components may be obtained by cooking (the herb in its raw form including all herb parts) and than concentrating the cooked material into a form of dry powder. The herbal components may also be extracted as tinctures, namely as liquid extracts which maintain the potency of the herb over time. The tinctures may be obtained as alcoholic extracts (e.g. of leaves or other plant material) or solutions of non-volatile substances. Generally, the alcohol is ethanol.

The herbal components may also be obtained using raw herbs and boiling them in water as in the preparation of a decoction, namely by boiling of dissolved plant material, which may include stems, roots, bark and rhizomes. Generally, according to the process of decoction the dissolved plant is boiled for 8-10 minutes in water (but shorter or longer boiling period may also be employed depending on the type of herb and its physical state) and is then strained.

The herbal components may also be used as commercially available.

The herbal components may be made into a concentrated dry powder form, where the powder may be either encapsulated or non-encapsulated. The herbs may be mixed together, wherein individual concentrated dry powders of each herb are admixed in varying ratios. A typical protocol for producing a concentrated dry powder of a certain herb involves extraction of the herb by boiling in a vat. A rotary extractor having a controlled temperature and timing may be employed in this process. Once extraction is completed the extract is exposed to low-temperature vacuum evaporation-concentration to yield a viscous liquid. The concentrated liquid is then piped into a flow coater, e.g., a granulator, which sprays the concentrate onto minute particles of a base material and dries them to create concentrated granules. The particles may be in a powder form of the extracted herb/s or may be particles of a natural material such as potato, cornstarch or similar materials. The granules may then be further treated, e.g., pressed into smooth tablets or used as concentrated powders.

Generally, the choice of a carrier, an excipient or a diluent may be dictated to some extent by the intended dosage form of the herbal formulation, the dosing regimen, the mode of administration and factors associated with the intended use and the subject to be treated. Herbal formulations may contain starch or may be starch-free.

The formulation of the invention may be formulated into a variety of solutions, emulsions, suspensions, powders, granules, natural and synthetic materials impregnated with the individual components of the herbal formulation, pills, capsules, tablets, cachets, pastilles, lozenges, bolus, electuary, pastes, ointments, creams, plasters, lotions, transdermal patches, suppositories and syrups.

In some embodiments, the herbal formulation of the invention is formulated for oral administration. Formulations suitable for oral administration may be presented in discrete units such as capsules, cachets or tablets each containing a predetermined amount of the herbal formulation; as a powder or granules; as a solution, a suspension or as an emulsion. The herbal formulation may also be presented as a bolus, electuary or paste. Tablets and capsules for oral administration may contain one or more carriers, binding agents, fillers, lubricants, disintegrants, and/or wetting agents. The tablets and capsules may be coated according to methods well known in the art.

Oral liquid preparations may, for example, be in the form of aqueous or oily suspensions, emulsions or syrups or may be presented as dry products, e.g., in a form of a powder or granules, for constitution with water or another suitable liquid vehicle, such as orange juice, e.g., immediately prior to use.

In an additional aspect of the invention, there is provided the use of any one formulation according to the invention in therapy. Thus, also contemplated is the use of a formulation of the invention in a method for treating a disease or a disorder.

The invention also provides the use of a formulation according to the invention in the preparation of a pharmaceutical or a neutraceutical composition. As will be further elaborated hereinbelow, the composition so prepared may be employed in the prevention (prophylaxis) and/or treatment of cancer, as an anticancer adjuvant to conventional modes of anticancer therapy (such as radiotherapy and chemotherapy), in improving at least one side effect associated with the treatment or prophylaxis of cancer, in the protection of bone marrow production of red blood cells and a variety of other therapeutic purposes.

Thus, in another aspect, the formulations of the invention are used in the prevention and/or treatment of cancer, as anticancer formulations or as adjuvants to conventional modes of anticancer therapy, such as radiotherapy and chemotherapy.

As used herein, "cancer" refers to any carcinoma, any sarcoma, tumors such as multiple myeloma, Waldenstroms' (IgM) gammapathy, and Bergers (IgA), CNS lymphoma (e.g., associated with AIDS), gonadal lymphomas and leukemias, mantle cell lymphomas, vascularized stages of leukemias (bone marrow) and lymphomas (in the lymph nodes), and any other leukemia or lymphoma, including low grade leukemias and lymphomas), solid tumors (i.e., vascularized tumors, including angiosarcomas, Kaposi's sarcoma, mesothelioma, Ewing's Sarcoma, choriocarcinoma, ascitis tumors such as ovarian cancer especially with peritoneal implants), gonadal cancers. (including ovarial and cervical), airway cancers (small cell lung, lung, and bronchial), gastrointestinal cancers (pancreatic, intestinal, colon, rectal, small intestinal, polyposis, gall duct, stomach), esophageal cancer, Barrett's esophagus cancer, oral cancer, parotid cancer, nasopharyngeal cancer, thyroid cancer, CNS cancers (glial, neuroblastoma multiforme, neuromas, meningiomas, astrocytomas, any other pediatric or adult CNS cancer), urogenital cancers (bladder, renal, adrenal, prostate), skin cancers (melanoma nodular, invasive, superficial spreading MF, squamous cell, lip) bone and connective tissue cancers (breast, bone, chondromas, leiomyomas, Wilm's tumor, retinoblastoma) and any other solid carcinoma or sarcoma of pediatric or adult patients.

In some embodiments, the cancer to be treated by the methods and formulations of the invention is selected from lung cancer, non small cell lung (NSCL) cancer, bronchioalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney, renal cell carcinoma, carcinoma of the renal pelvis, mesothelioma, hepatocellular cancer, biliary cancer, chronic or acute leukemia, lymphocytic lymphomas, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenomas, including refractory versions of any of the above cancers, or a combination of one or more of the above cancers.

In further embodiments, the cancer is breast cancer which is not limited to any stage, grade, histomorphological feature, invasiveness, aggressiveness or malignancy of the affected tissue or cell aggregation.

In some embodiments, the breast cancer is stage 0 breast cancer, stage I breast cancer, stage II breast cancer, stage HI breast cancer, stage FV breast cancer, grade I breast cancer, grade II breast cancer, grade III breast cancer, malignant breast cancer, primary carcinomas of the breast, and all other types of cancers, malignancies and transformations associated with the breast.

The invention also provides a use of a formulation of the invention in improving at least one side effect associated with the treatment or prophylaxis of a disease or disorder such as cancer. In some embodiments, a formulation of the invention is used in the treatment or prevention of side effects associated with, e.g., chemotherapy, specifically systemically administered chemotherapy. Such side effects may be one or more of loss of appetite, loss of sleep, fatigue, neutropenia, reduction in daily activity, decline in overall feeling, depression, digestive dysfunction, dysgeusia, anemia, weakness, pain, and impaired daily function, nausea and vomiting and combinations thereof.

The formulations of the invention have been demonstrated to prevent and/or treat side effects associated with administered chemotherapeutic agents; the formulations of the invention neither abrogate nor attenuate the therapeutic effect of the administered chemotherapy, thereby permitting such effective use of therapeutic dosage levels. In other words, the formulations of the invention when used along with traditional chemotherapy do not bring about a reduction in the anticancer therapeutic effect imposed by the chemotherapeutic agent, thereby permitting a maximum effect at the tissue desired to be treated with a reduction or complete elimination of side effects which are associated with the treatment.

The formulations of the invention may be administered in conjunction with the administration of chemotherapy to the patient. In some embodiments, a formulation according to the invention is administered prior to the administration of the chemotherapy. The formulation may be administered on a single day or on several days prior to chemotherapy.

In other embodiments, the formulation of the invention is administered following administration of the chemotherapeutic agent.

In still other embodiments, the formulation is administered prior to and subsequent to the administration of a chemotherapeutic agent and may optionally take place on one or multiple days prior to and one or multiple days subsequent to the chemotherapy.

In other embodiments administration of the formulation of the invention starts before the initiation of chemotherapy and continues throughout the duration of chemotherapy.

The administration of the formulation of the invention may be once daily or on the day of administration or multiple times a day.

In some embodiments, the formulation is administered orally three times a day prior to, during and/or subsequent to chemotherapy.

The side effects to be minimized or prevented may be associated with any one or more radiotherapy or any one or more chemotherapeutic agent such as, but not limited to, 5-FU, Altretamine, Bleomycin, Busulfan, Capecitabine, Carboplatin, Carmustine, Chlorambucil, Cisplatin, Cladribine, Crisantaspase, Cyclophosphamide, Cytarabine, Dacarbazine, Dactinomycin, Daunorubicin, Docetaxel, Doxorubicin, Epirubicin, Etoposide, Fludarabine, Fluorouracil, Gemcitabine, Hydroxycarbamide, Idarubicin, Ifosfamide, Irinotecan, Liposomal doxorubicin, Leucovorin, Lomustine, Melphalan, Mercaptopurine, Mesna, Methotrexate, Mitomycin, Mitoxantrone, Oxaliplatin, Paclitaxel, Pemetrexed, Pentostatin, Procarbazine, Raltitrexed, Streptozocin, Tegafur-uracil, Temozolomide, Thiotepa, Tioguanine/Thioguanine, Topotecan, Treosulfan, Vinblastine, Vincristine, Vindesine, Vinorelbine, Bleomycin, Busulfan, Capecitabine, Carboplatin, Carmustine, Chlorambucil, Cisplatin, Cladribine, Crisantaspase, Cyclophosphamide, Cytarabine, Dacarbazine, Dactinomycin, Daunorubicin, Docetaxel, Doxorubicin, Epirubicin, Etoposide, Fludarabine, Fluorouracil, Gemcitabine, Hydroxycarbamide, Idarubicin, Ifosfamide, Irinotecan, Liposomal doxorubicin, Leucovorin, Lomustine, Melphalan, Mercaptopurine, Methotrexate, Mitomycin, Mitoxantrone, Oxaliplatin, Paclitaxel, Pemetrexed, Pentostatin, Procarbazine, Raltitrexed, Streptozocin, Tegafur-uracil, Temozolomide, Thiotepa, Tioguanine-Thioguanine, Topotecan, Treosulfan, Vinblastine, Vincristine, Vindesine, Vinorelbine and any combination of any two or more of these agents.

In some embodiments, the chemotherapeutic agent is selected from a combination of doxorubicin, cyclophosphamide and paclitaxel and a combination of doxorubicin, cyclophosphamide and 5-fluorouracil.

In other embodiments, the chemotherapeutic agent is a combination of doxorubicin, cyclophosphamide and 5-fluorouracil.

In further embodiments, the chemotherapeutic agent is a combination of doxorubicin, cyclophosphamide and paclitaxel.

In still further embodiments, said chemotherapeutic agent is a combination of doxorubicin, cyclophosphamide and docetaxel.

In still yet further embodiments, where the chemotherapeutic agent is administered in conjunction with a hormonal treatment (for example tamoxifen) and/or biological treatment (such as Herceptin), the formulation of the invention may be administered in consideration of the hormonal or biological treatment, similarly to the defined above with reference to administration methods and regimen, or independently thereof.

Without wishing to be bound by theory, the administration of a formulation according to the invention, as disclosed, brings about the reduction in the severity of post-chemotherapy side effects and increases the quality of life experienced by patients receiving chemotherapy. However, it is not only the side effect which contributes to the overall ill state of the subject being treated, it is also the injury caused by such therapy to normal tissues. In fact, the successful use of chemotherapeutic agents to treat cancer depends upon the differential killing effect of the chemotherapeutic agent on cancer cells compared to its effect on normal tissues.

One considerable effect is on the killing of cells associated with the manufacture of red blood cells. Acute and chronic bone marrow toxicities are a major limiting factor in the treatment of cancer. The formulations of the invention have been shown to be protective of bone marrow production of red blood cells.

Thus, the formulations of the invention are also provided for the treatment of a disorder associated with a deficient red blood cell production. The invention also provides formulations for the protection of bone marrow production of red blood cells during and/or post chemotherapy or radiotherapy.

The disorder associated with a deficient red blood cell production may be selected, in a non-limiting fashion, from autoimmune diseases or a malignancies, beta-thalassemia, cystic fibrosis, early anemia of prematurity, anemia associated with chronic inflammatory disease, spinal cord injuries, acute blood loss, aging and neoplastic disease states.

In some embodiments, the deficiency in the production of red blood cells is associated with chemotherapy.

The invention thus provides, in another one of its aspects, a method for improving the well being or quality of life of a subject, said method comprising administering to the subject an effective amount of a formulation according to the invention.

According to another aspect of the present invention there is provided a method of preventing and/or treating a disease or disorder in a subject suffering or having predisposition to suffering therefrom, the method comprising administering to the subject a therapeutically effective amount of a herbal formulation according to the invention.

In some embodiments, said disease or disorder is cancer, as defined above. In some embodiments, said cancer is breast cancer. In further embodiments, said cancer is breast cancer.

In some embodiments, the subject suffering from said disease or disorder is a mammal, including human (males and/or females) and non-human subjects. In some embodiments, the subject is a female subject. In other embodiments, the subject is a male subject. In some embodiments, where the disease is breast cancer, the subject is a female subject.

The invention further provides a method for preventing or minimizing at least one side effect associated with chemotherapy, the method comprising administering a therapeutically effective amount of at least one formulation according to the invention to a subject prior to, subsequent to or simultaneous with the administration of chemotherapy.

The invention also provides a method for the protection of bone marrow in the course of anti-cancer treatment by chemotherapy, the method comprising administering a therapeutically effective amount of at least one formulation according to the invention prior to, subsequent to or simultaneous with the administration of chemotherapy.

The term "prevention (or prophylaxis) and/or treatment", or any lingual variation thereof, as used herein refers to the administering of a therapeutic amount of a formulation of the present invention which is effective to ameliorate undesired symptoms associated with a disease, to prevent the manifestation of such symptoms before they occur, to slow down the progression of the disease, slow down the deterioration of symptoms, to enhance the onset of remission period, slow down the irreversible damage caused in the progressive chronic stage of the disease, to delay the onset of said progressive stage, to lessen the severity or cure the disease, to improve survival rate or more rapid recovery, or to prevent the disease form occurring or a combination of two or more of the above.

The "effective amount" for purposes herein is determined by such considerations as may be known in the art. The amount should be effective to achieve the desired therapeutic effect as described herein, depending, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the ligand to the receptor, its distribution profile within the body, a variety of pharmacological parameters such as half life in the body, on undesired side effects, if any, on factors such as age and gender, etc.

The invention also provides in another of its aspects a kit or a commercial package comprising a premixed formulation according to the invention and instructions for use. In other embodiments, the kit comprises a plurality of compartments or receptacles (e.g., bottles or vials), each comprising a single or a selection of herbs, a mixing means (e.g., a mixing container and a spatula) for mixing the herbs and instructions for use.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Additionally, the phrases "ranging/ranges between" a first indicated number and a second indicated number and "ranging/ranges from" a first indicated number "to" a second indicated number are used herein interchangeably and are meant to include the first and second indicated numbers and all fractional and integral numerals therebetween. The term "about" as used herein indicates that the first and second numbers defining the range may in fact be 10% above or below the indicated limits. For example, the expression "ranging between about 1 and 30%" refers to a concentration of between 1%±10% to 30%±10% (wt % of the total wt of the formulation) and any concentration therebetween. The expression "about 1-30%" similarly refers to a concentration between 1%±10% to 30%±10% (wt % of the total wt of the formulation) and any concentration therebetween.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 7A shows an image of a control sample. FIG. 7B shows an image of cells treated with 3 mg/ml of a formulation of the invention; and FIG. 7C shows an image of cells treated with 50 mg/ml of a formulation of the invention, FIG. 8A shows analysis of a control sample; FIG. 8B shows an analysis of cells treated with 3 mg/ml of a formulation of the invention; and FIG. 8C shows the results of the analysis of cells treated with 50 mg/ml of a formulation of the invention.

DETAILED DESCRIPTION OF EMBODIMENTS

Figure 1:
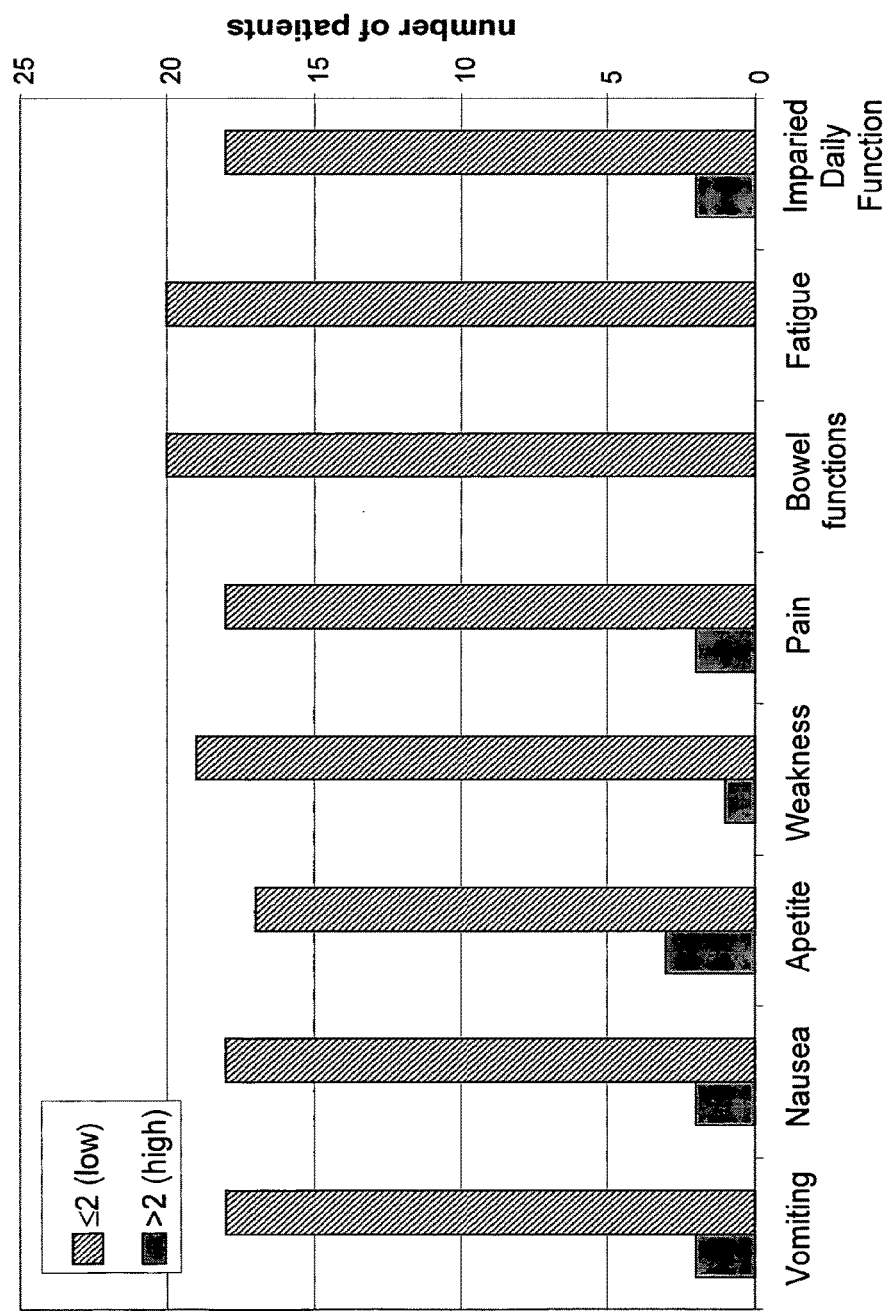
FIG. 1 is a bar graph presenting the analysis of quality of life of the combined treatment according to the present embodiments.

The present invention, in most general terms, relates to uniquely designed herbal formulations and, more particularly, but not exclusively, to herbal formulations that are suitable as complementary therapy for cancer patients.

It is to be understood that the invention is not necessarily limited in its application to the details set forth in the following description or exemplified by the Examples, as these are provided only as non-limiting examples of the broad aspects of the invention. The invention is capable of other embodiments or of being practiced or carried out in various ways.

As demonstrated herein, the formulations of the invention have been found to be highly efficacious when used in combination with chemotherapy, in reducing multiple side effects induced by the chemotherapy and in shielding the production of red blood cells, white blood cells and neutrophils from the toxic effects of chemotherapy.

Chemotherapy-induced nausea and vomiting (CINV) is a common and serious problem encountered by many patients receiving anti-cancer therapy. Up to three fourths of all cancer patients experience chemotherapy-related emesis. CINV complicates or prevents administration of planned therapy and decreases quality of life. Although new agents, such as palonosetron and aprepitant, have improved outcomes, CINV is still a major concern for many patients. In older studies patients receiving chemotherapy reported nausea as the most severe symptom and vomiting as the fifth. Patients who do not receive preventive therapy have a 70% to 90% incidence of delayed emesis with high-risk agents (e.g., Adriamycine and Cyclophosphamide) and a 30% to 60% risk with moderate-risk agents (Taxol).

In the studies disclosed herein, on subjects being treated according to methodologies of the invention, 90% of the patients suffered minor or no vomiting at all. Minor or no nausea has been noted in a very small number of patients, needing no supplementary conventional medication, except the dose in the treatment days.

Febrile neutropenia (FN) is a severe clinical outcome that justifies the use of colony stimulating factor (CSFs) when the risk of FN is approximately 20% and no other equally effective regimen that does not require CSFs is available. Current evidence indicates that primary prophylaxis with a CSF results in a relative risk reduction of FN by approximately 50%. Significant reductions in documented infections have also been demonstrated. An analysis of five trials that have reported infection-related mortality failed to find a significant reduction with CSF support [summary odds ratio, 0.60 (0.30, 1.22); P=0.16]. However, the power of the combined analysis was insufficient to determine this outcome. An additional outcome demonstrated in these trials was the maintenance of dose intensity of the chemotherapeutic regimen through avoidance of dose reduction or delay secondary to neutropenia. The study reported significant reductions in the risk of FN from 37% to 20% (14 studies, n=3,091, relative risk reduction 46%, P<0.0001) and the risk of infection-related mortality from 3.3% to 1.7% (10 studies, n=2,468, relative risk reduction 48%, P=0.01).

In studies described herein, employing methodologies of the invention, 80% of the patients treated with a formulation of the invention did not need to take growth factor drugs to enhance white blood or red blood count. In the majority of the cases blood production was maintained substantially stable throughout the chemotherapy.

Cancer treatments may interfere with the patient's ability to taste, ingest, swallow or digest food. Drugs may cause nausea, diarrhea, and anorexia. Although many new agents have been developed to combat these side effects, patients still suffer greatly during treatment. One of the major side effects presenting a significant challenge to the cancer patient is alteration of taste, or dysgeusia.

Chemotherapeutic drugs are secreted or excreted in tears, saliva, sweat, bile, or urine. Drugs in the saliva may markedly alter taste (dysgeusia), leading to food revulsion and avoidance. After early satiety, dysgeusia is the most common challenge in patients on chemotherapy.

The two main types of dysgeusia are loss of taste acuity and distortion of taste. Loss of taste acuity comes from drug inhibition of a taste receptor function. Taste distortion results from drugs activating the taste receptor in an abnormally persistent fashion or preventing activation of the receptor The treatment of dysgeusia is typically very difficult. Treatment with agents such as zinc, folic acid, α-lipoic acid, and vitamins of the "B" class may alleviate some of the metallic taste but are only mildly helpful. Zinc seems to work best with a "sweet" dysgeusia. Drugs such as antracyclines and taxanes may have the worst associated dysgeusia. These seem to be secreted in the saliva and after the first bite or chew often produce a horrible taste sensation. After drug cessation, the taste returns to normal over a period of 2 months.

In studies described herein, employing methodologies of the invention, 85% of patients reported no or minor decrease in appetite and no patient reported a digestive dysfunction or dysgeusia.

Fatigue was reported in 20% of 430 assessable patients receiving adjuvant chemotherapy (202 standard-doses, 228 high-doses) with at least a 3-year follow-up, without change over time or difference between treatment arms. Mean Hb levels were lower following high-dose chemotherapy. Only 5% of patients experienced fatigue and anemia. Mental health score was the strongest fatigue predictor at all assessment moments. Menopausal status had no effect on fatigue. Linear mixed effect models showed that the higher the Hb level (P=0.0006) and mental health score (P<0.0001), the less fatigue was experienced. Joint (P<0.0001) and muscle pain (P=0.0283) were associated with more fatigue.

In conclusion of this study, within the patients being treated with a formulation of the invention, no patient reported severe fatigue.

In conclusion, the results demonstrate that the herbal formulation treatment according to the present invention is safe and serves as an effective adjunctive therapy to ameliorate multiple side effects of chemotherapy and to enhance the immune system in cancer patients.

An exemplary formula comprises the following herbal powder extracts: Astragalus Membranaceus (Huang Qi), Poriae Cocos (Fu Ling), Atractylodes Macrocephala (Bai zhu), Lycium Chinense (Gou Qi Zi), Ligustrum Lucidum (Niu Zhen Zhi), Paeonia Lactiflora (Bai Shao), Paeonia Obovata (Chi Shao), Citrus Reticulata (Chen Pi), Ophiopogon Japonicus (Mai men Dong), Milletia Reticulata (Ji Xue Teng), Oldenlandia Diffusa (Bai Hua She She cao), Scutellaria Barbata (Ban Zhi Lian), Prunella Vulgaris (Xia Ku Cao), Glehnia Littoralis (Bei Sha Shen), as described herein.

Additional herbs that can be added into the formula include, for example, Radix Pseudostellariae Heterophyllae (Tai Zhi Shen), Radix Glycyrrhizae (Gan Cao), Massa Fermentata (Shen Qu) and Fructus Hordei Germinatus (Mai Ya).

Reference is now made to the following examples, which together with the above description illustrate some embodiments of the invention in a non limiting fashion.

Formulations of the Invention:

The herbs used were encapsulated dried herbal extract powders. The herbal formula was prescribed in the dosage of 6 grams (2 grams×3 times a day).

The extracted herbal powders where imported under license in accordance with the regulations of the Israel Ministry of Health by "ZEN" Herb Company (Tel Aviv, Israel) and manufactured under GMP conditions. The placebo capsules where provided by the same company resembling the CHT capsules in taste, texture and appearance.

A variety of formulations have been prepared and used. The following is a description of a group of formulations prepared according to the invention.

TABLE 1

Formulation 1.

| | Latin name | Chinese name | grms | Wt % |
|---|---|---|---|---|
| 1 | Astragalus Membranaceus | Huang QI | 10 | 8.1 |
| 2 | Poriae Cocos | Fu Ling | 6 | 4.9 |
| 3 | Atractylodes Macrocephala | Bai zhu | 6 | 4.9 |
| 4 | Lycium Chinense | Gou Qi Zi | 8 | 6.5 |
| 5 | Ligustrum Lucidum | Niu Zhen Zhi | 10 | 8.1 |
| 6 | Paeonia Lactiflora | Bai Shao | 8 | 6.5 |
| 7 | Paeonia Obovata | Chi Shao | 6 | 4.9 |
| 8 | Glehnia Littoralis | Bei Sha Shen | 8 | 6.5 |
| 9 | Citrus Reticulata | Chen Pi | 6 | 4.9 |
| 10 | Ophiopogon Japonicus | Mai men Dong | 8 | 6.5 |
| 11 | Milletia Reticulata | Ji Xue Teng | 10 | 8.1 |
| 12 | Oldenlandia Diffusa | Bai Hua She She cao | 15 | 12.2 |
| 13 | Scutellaria Barbata | Ban Zhi Lian | 12 | 9.8 |
| 14 | Prunella Vulgaris | Xia Ku Cao | 10 | 8.1 |

As regards the formulations of the invention, additional herbs were used for particular individual symptoms; these include one or more of the following exemplary herbs: Radix Pseudostellariae Heterophyllae (Tai Zhi Shen), Radix Glycyrrhizae (Gan Cao), Massa Fermentata (Shen Qu) and Fructus Hordei Germinatus (Mai Ya), utilized in case of digestive disorders. Any other herb mentioned herein with reference to any one particular formulation may also be added to a formulation not indicated to comprise same.

TABLE 2

Formulation 2.

| | Latin name | Chinese name | Grms | Wt % |
|---|---|---|---|---|
| 1 | *Astragalus Membranaceus* | Huang Qi | 20 | 12.4 |
| 2 | *Atractylodes Macrocephala* | Bai zhu | 10 | 6.2 |
| 3 | *Redix Glycyrrhizae Uralensis* | Gan Cao | 4 | 2.5 |
| 4 | *Poriae Cocos* | Fu Ling | 8 | 5.0 |
| 5 | *Lycium Chinense* | Gou Qi Zi | 12 | 7.5 |
| 6 | Radix *Paeoniae Lactiflorae* | Bai Shao | 10 | 6.2 |
| 7 | *Paeonia Obovata* | Chi Shao | 8 | 5.0 |
| 8 | *Curcumae*, Tuber | Yu Jin | 10 | 6.2 |
| 9 | *Citrus Reticulata* | Chen Pi | 6 | 3.7 |
| 10 | *Ligustrum Lucidum* | Niu Zhen Zhi | 15 | 9.3 |
| 11 | *Oldenlandia Diffusa* | Bai Hua She She cao | 15 | 9.3 |
| 12 | *Scutellaria Barbata* | Ban Zhi Lian | 20 | 12.4 |
| 13 | *Prunella Vulgaris* | Xia Ku Cao | 15 | 9.3 |
| 14 | *Anemarrhenae Asphodeloidis* Rhizoma | Zi Mu | 8 | 5.0 |

TABLE 3

Formulation 3.

| | Latin name | Chinese name | Grms | Wt % |
|---|---|---|---|---|
| 1 | *Atractylodes Macrocephala* | Bai zhu | 10 | 5.8 |
| 2 | *Pseudostellaiae Heterophillae* | Tai Zi Shen | 15 | 8.7 |
| 3 | *Poriae Cocos* | Fu Ling | 12 | 7.0 |
| 4 | Radix *Paeoniae Lactiflorae* | Bai Shao | 12 | 7.0 |
| 5 | Radix *Angelica Sinensis* | Dang Gui | 15 | 8.7 |
| 6 | *Paeonia Obovata* | Chi Shao | 8 | 4.7 |
| 7 | Radix Et Caulis Jixueteng | Ji Xue Tang | 12 | 7.0 |
| 8 | *Cyperi Rotundi Rhizoma* | Xiang Fu | 8 | 4.7 |
| 9 | *Ligustrum Lucidum* | Niu Zhen Zhi | 10 | 5.8 |
| 10 | *Ophiopogon Japonicus* | Mai men Dong | 10 | 5.8 |
| 11 | *Scutellaria Barbata* | Ban Zhi Lian | 20 | 11.6 |
| 12 | Radix Isatidis Seu Baphicacanthi | Ban Lan Gen | 15 | 8.7 |
| 13 | *Prunella Vulgaris* | Xia Ku Cao | 15 | 8.7 |
| 14 | *Anemarrhenae Asphodeloidis* Rhizoma | Zi Mu | 10 | 5.8 |

TABLE 4

Formulation 4.

| | Latin name | Chinese name | Grms | Wt % |
|---|---|---|---|---|
| 1 | *Atractylodes Macrocephala* | Bai zhu | 8 | 4.7 |
| 2 | Ginseng Radix | Ren Shen | 20 | 11.8 |
| 3 | *Poriae Cocos* | Fu Ling | 10 | 5.9 |
| 4 | *Lycium Chinense* | Gou Qi Zi | 12 | 7.1 |
| 5 | Radix *Angelica Sinensis* | Dang Gui | 15 | 8.9 |
| 6 | *Paeonia Obovata* | Chi Shao | 8 | 4.7 |
| 7 | Radix *Salviae Miltiorrhizae* | Dan Shen | 12 | 7.1 |
| 8 | Radix Et Caulis Jixueteng | Ji Xue Tang | 10 | 5.9 |
| 9 | *Citrus Reticulata* | Chen Pi | 6 | 3.6 |
| 10 | *Glehnia Littoralis* | Bei Sha Shen | 8 | 4.7 |
| 11 | *Panacis Quinquefolii*, Radix | Xi Yang Shen | 10 | 5.9 |
| 12 | *Flos Lonicerae Japonicae* | Jin Yin Hua | 12 | 7.1 |
| 13 | *Pseudobulbus Shancigu* | Shan Ci Gu | 18 | 10.7 |
| 14 | *Prunella Vulgaris* | Xia Ku Cao | 20 | 11.8 |

TABLE 5

Formulation 5.

| | Latin name | Chinese name | Grms | Wt % |
|---|---|---|---|---|
| 1 | *Atractylodes Macrocephala* | Bai zhu | 6 | 3.5 |
| 2 | Radix *Codonopsitis Pilosulae* | Dang Shen | 12 | 6.9 |
| 3 | *Poriae Cocos* | Fu Ling | 6 | 3.5 |
| 4 | *Lycium Chinense* | Gou Qi Zi | 15 | 8.7 |

TABLE 5-continued

Formulation 5.

| | Latin name | Chinese name | Grms | Wt % |
|---|---|---|---|---|
| 5 | Radix *Paeoniae Lactiflorae* | Bai Shao | 12 | 6.9 |
| 6 | Radix *Salviae Miltiorrhizae* | Dan Shen | 10 | 5.8 |
| 7 | Radix Et Caulis Jixueteng | Ji Xue Tang | 15 | 8.7 |
| 8 | Curcumae Tuber | Yu Jin | 18 | 10.4 |
| 9 | *Curcuma Zedoaria* | E-Zhu | 15 | 8.7 |
| 10 | *Aucklandiae Lappae* Radix | Mu Xiang | 12 | 6.9 |
| 11 | *Ligustrum Lucidum* | Niu Zhen Zhi | 12 | 6.9 |
| 12 | *Smilacis Glabrae*, Rhizoma | Tu Fu Ling | 15 | 8.7 |
| 13 | *Pseudobulbus Shancigu* | Shan Ci Gu | 15 | 8.7 |
| 14 | *Anemarrhenae Asphodeloidis* Rhizoma | Zi Mu | 10 | 5.8 |

TABLE 6

Formulation 6.

| | Latin name | Chinese name | Grms | Wt % |
|---|---|---|---|---|
| 1 | *Astragalus Membranaceus* | Huang Qi | 20 | 11.2 |
| 2 | *Atractylodes Macrocephala* | Bai zhu | 12 | 6.7 |
| 3 | *Poriae Cocos* | Fu Ling | 8 | 4.5 |
| 4 | Radix *Angelica Sinensis* | Dang Gui | 12 | 6.7 |
| 5 | Radix Salviae Miltiorrhizae | Dan Shen | 10 | 5.6 |
| 6 | Radix Et Caulis Jixueteng | Ji Xue Tang | 10 | 5.6 |
| 7 | Curcumae Tuber | Yu Jin | 12 | 6.7 |
| 8 | *Aucklandiae Lappae* Radix | Mu Xiang | 8 | 4.5 |
| 9 | Sangjisheng, Ramulus | Sang Zi Sheng | 10 | 5.6 |
| 10 | *Panacis Quinquefolii*, Radix | Xi Yang Shen | 15 | 8.4 |
| 11 | Radix Isatidis Seu Baphicanthi | Ban Lan Gen | 18 | 10.1 |
| 12 | *Flos Lonicerae Japonicae* | Jin Yin Hua | 15 | 8.4 |
| 13 | *Prunella Vulgaris* | Xia Ku Cao | 20 | 11.2 |
| 14 | *Anemarrhenae Asphodeloidis* Rhizoma | Zi Mu | 8 | 4.5 |

TABLE 7

Formulation 7.

| | Latin name | Chinese name | Grms | Wt % |
|---|---|---|---|---|
| 1 | *Pseudostellaiae Heterophillae* | Tai Zi Shen | 15 | 8.5 |
| 2 | Herba *Lobeliae Chinensis Cum Radice* | Ban Bian Lian | 10 | 5.7 |
| 3 | *Rhizoma Alismatis* | Ze Xie | 8 | 4.5 |
| 4 | *Rhemanniae Glutinosae Conquitae* Radix | Shu Di Huang | 12 | 6.8 |
| 5 | Persicae Semen | Tao Ren | 12 | 6.8 |
| 6 | *Curcuma Zedoaria* | E-Zhu | 15 | 8.5 |
| 7 | Diospyri Kaki Calyx | Xi Di | 8 | 4.5 |
| 8 | Radix Adenophorae Seu Glehniae | Sha Shen | 12 | 6.8 |
| 9 | Sophorae Subprostratae Radix | Shan Dou Gen | 15 | 8.5 |
| 10 | *Pseudobulbus Shancigu* | Shan Ci Gu | 12 | 6.8 |
| 11 | Rhizoma, Phragmitis Communis | Lu Gen | 15 | 8.5 |
| 12 | *Gardeniae Jasminoidis Fructus* | Zhi Zi | 12 | 6.8 |
| 13 | *Nelumbinis Nuciferae* Semen | Lian Xin | 12 | 6.8 |
| 14 | Herba Lophatheri Gracilis | Dan Zhu Ye | 18 | 10.2 |

TABLE 8

Formulation 8.

| | Latin name | Chinese name | Grms | Wt % |
|---|---|---|---|---|
| 1 | Radix Codonopsitis Pilosulae | Dang Shen | 12 | 6.9 |
| 2 | *Pseudostellaiae Heterophillae* | Tai Zi Shen | 15 | 8.6 |
| 3 | *Coicis Lachryma-jobi* Semen | Yi Yi Ren | 12 | 6.9 |
| 4 | Semen Plantaginis | Che Qian Zi | 10 | 5.7 |

TABLE 8-continued

Formulation 8.

| | Latin name | Chinese name | Grms | Wt % |
|---|---|---|---|---|
| 5 | Arilus Euphoriae Longanae | Long Yang Rao | 8 | 4.6 |
| 6 | Mori Albae Fructus | Sang Shen | 18 | 10.3 |
| 7 | Paeonia Obovata | Chi Shao | 8 | 4.6 |
| 8 | Persicae Semen | Tao Ren | 6 | 3.4 |
| 9 | Cyperi Rotundi Rhizoma | Xiang Fu | 8 | 4.6 |
| 10 | Plastrum, Testudinis | Gui Ban | 15 | 8.6 |
| 11 | Panacis Quinquefolii, Radix | Xi Yang Shen | 15 | 8.6 |
| 12 | Taraxaci Mongolici Cum Radice Herba | Pu Gong Yin | 18 | 10.3 |
| 13 | Sophorae Subprostratae Radix | Shan Dou Gen | 12 | 6.9 |
| 14 | Prunella Vulgaris | Xia Ku Cao | 18 | 10.3 |

TABLE 9

Formulation 9.

| | Latin name | Chinese name | Grms | Wt % |
|---|---|---|---|---|
| 1. | Radix Codonopsitis Pilosulae | Dang Shen | 20 | 11.6 |
| 2 | Herba Lobeliae Chinensis Cum Radice | Ban Bian Lian | 12 | 6.9 |
| 3 | Fructus Kochia S copariae | Di Fu Zi | 10 | 5.8 |
| 4 | Mori Albae Fructus | Sang Shen | 10 | 5.8 |
| 5 | Flos Carthami Tinctorii | Homg Hua | 8 | 4.6 |
| 6 | Persicae Semen | Tao Ren | 8 | 4.6 |
| 7 | Diospyri Kaki Calyx | Xi Di | 12 | 6.9 |
| 8 | Citri Aurantii Fructus | Zhi Ke | 10 | 5.8 |
| 9 | Citri Aurantii Fructus Immaturus | Zhi Shi | 10 | 5.8 |
| 10 | Plastrum, Testudinis | Gui Ban | 18 | 10.4 |
| 11 | Smilacis Glabrae, Rhizoma | Tu Fu Ling | 20 | 11.6 |
| 12 | Pseudobulbus Shancigu | Shan Ci Gu | 15 | 8.7 |
| 13 | Gardeniae Jasminoidis Fructus | Zhi Z | 10 | 5.8 |
| 14 | Herba Lophatheri Gracilis | Dan Zhu Ye | 10 | 5.8 |

Study Design and Subjects:

Breast cancer patients receiving formulation 1 of the invention in concurrent with chemotherapy, were reviewed over a period of 3 years. The patients aged 18-70, having localized tumors, exhibited Karnovsky performance status >80% and were candidates for adjuvant or neodajuvant chemotherapies with anthracyclines-based combination with or without taxanes at the Sorasky Oncology department Center. All patients had biopsy proven disease, were chemonaive and had normal liver and kidney function (up to X2 of ULN values) with initial blood count: Hb>10, WBC>3000, platelets>100,000. Thus, all patients included in this study were treated in parallel by conventional chemotherapy in oncology departments at academic conventional hospitals. The content of the herbal formulation was never made known to them or made public at the termination of the study.

Treatment Applied:

Chemotherapy applied to patients was adjuvant or neoadjuvant standard protocol for breast cancer treatment, which, in the majority of the tested patients, included a combination of doxorubicin (Adriamycine), cyclophosphamide (Cytophosphan) and paclitaxel (Taxol) (AC+T) or doxorubicin (Adriamycine), cyclophosphamide (Cytophosphan) and 5-fluorouracil (5-FU) (CAF). The chemotherapy was applied according to a typical and well-known international chemotherapy protocols, as follows:

1. Four treatments of Adriamycine 60 mg/m$^2$ and Cytophosphan 600 mg/m$^2$, every 3 weeks for 4 cycles (AC protocol).

2. Four treatments of Adriamycine 60 mg/m$^2$ and Cytophosphan 600 mg/m$^2$, every 3 weeks for 4 cycles, followed by Taxol 80 mg/m$^2$, every week for 12 weeks (AC+T protocol).

3. Three cycles of Cytophosphan 500 mg/m$^2$, Adriamycine 50 mg/m$^2$ and 5-FU 500 mg/m$^2$, every 3 weeks for 6 cycles (CAF protocol).

4. Dose dense AC every 2 weeks followed by paclitaxel 175 mg/m$^2$ every 2 weeks, with WBC stimulants (Neupogen/Neulastim) support (dd. AC+T protocol).

Patients treated with one of first 2 regimens received Epirubicin 90 mg/m$^2$ substituting Adriamycin at the discretion of attending physician.

Following enrollment, patients were blindly randomized to receive either capsules containing a formulation according to the invention (typically formulation 1) or placebo capsules. Capsules containing formulation 1 or an equivalent according to the invention contained an effective amount of a homogeneous mixture of herbal extract powders. The extracted herbal powders where imported under license as described above.

Example 1

The records from 20 consecutive breast cancer patients, having been treated with formulation 1 of the invention or an equivalent thereof, in parallel with conventional therapy, were analyzed for the study. Table 10 lists the baseline characteristics of these patients.

TABLE 10

Baseline data on patients receiving adjuvant treatment in conjunction with chemotherapy. Values are numbers (percentages) of participants unless otherwise indicated.

| Baseline Data | Patients |
|---|---|
| Number | 20 |
| Mean age, years (SD) | 52.64 (±2.08) |
| Body weight | 65.47 (±3.75) |
| BRCA 1/2 | 4 (20%) |
| Cancer + Stage | |
| IDC grade 2-3 | 16 (80%) |
| ILC | 2 (10%) |
| DCIS | 1 (5%) |
| Metastatic cancer | 1 (5%) |
| Treatment protocols | |
| AC | 5 (25%) |
| AC + T | 7 (35%) |
| CAF | 5 (25%) |
| Other* | 3 (15%) |

*Other protocols included: CEF + taxotere, CEF + taxol.

Analysis of post-treatment scores, presented in FIG. 1, showed low scores of chemotherapy side-effects in the categories of vomiting (Avg=0.9), nausea (Avg=1.15), appetite (Avg=1.3), weakness (Avg=1.25), pain (Avg=0.7), bowel function (Avg=0.75), fatigue (Avg=1.3) and impaired daily function (Avg=1.25). As presented in FIG. 1, the majority of the patients treated with formulation 1 of the invention demonstrated reduced incidence of the various side effects.

Figure 2:
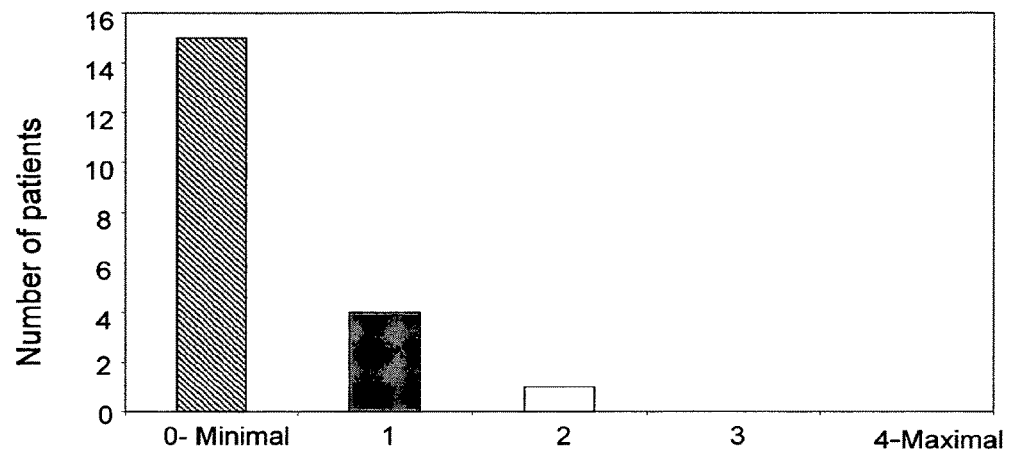
FIG. 2 is a bar representation showing the number of studied patients receiving growth factor drugs to enhance white blood or red blood count.

Since low scores of white blood cells (WBC), in particular, but sometimes also of red blood cells (RBC) is a common side effect of chemotherapy to breast cancer patients, the need for using growth factor drugs to enhance white blood or red blood count was also evaluated. As depicted in FIG. 2, the majority of patients did not require treatment with growth factor drugs; therefore, attesting to the ability of the formulation of the invention to effect maintenance and protection of blood cells production.

Figure 3:
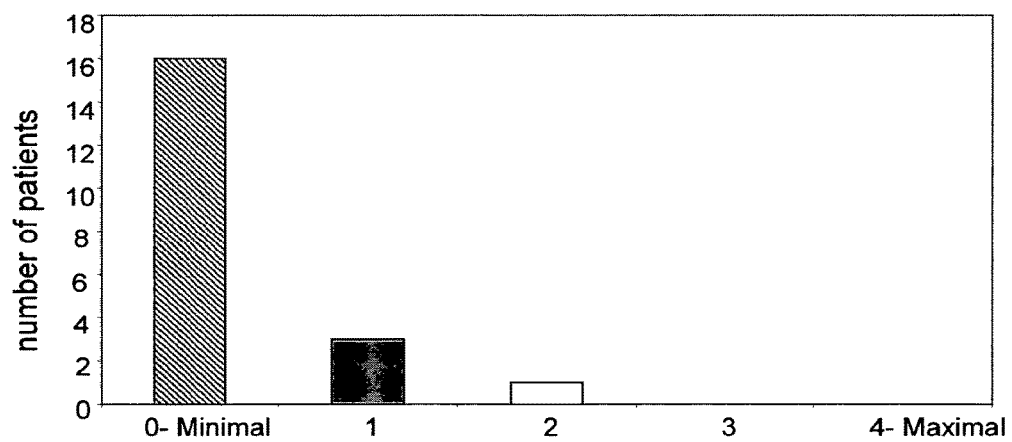
FIG. 3 is a bar representation showing the number of studied patients in which a delay in chemotherapy was affected.

The delay in chemotherapy treatment according to the clinical benefit questionnaires was also tested as means to understanding the effect of the formulation of the invention on the overall ability of a patient to undergo chemotherapy while being treated with a formulation of the invention. As shown in FIG. 3, out of 20 patients, only 3 patients reported delay in one treatment and one patient reported delay in two treatments. The majority of the patients were able to sustain the scheduled regimen and drug doses when treated also with the formulation of the invention, thereby increasing success for treatment.

Importantly, no herbal-related adverse effects were reported at any time.

The results of this study demonstrated that the use of the formulations described herein was effective in alleviating side effects of breast cancer patients receiving chemotherapy.

In summary, the formulations of the invention have been shown to act as adjunctive treatment to ameliorate multiple side effects of chemotherapy, as follows:

Vomiting and nausea: It is shown (FIG. 1) that 90% of the patients had minor or no vomiting at all. Minor or no nausea has been noted in very few patients, without any need for supplementary conventional medication (in addition to the applied chemotherapy).

Febrile neutropenia (FN): There have been no reports of FN during the study.

Use of growth factor drugs: Only four patients (20%) reported the need to take growth factor drugs to enhance white blood or red blood count.

Alteration of taste (dysgeusia): In this study, 85% of patients reported no or minor decrease in appetite and no patient reported any significant digestive dysfunction or dysgeusia.

Fatigue: The results demonstrate that none of the patients receiving the formulation of the invention reported severe fatigue.

This study demonstrates that herbal formulation treatments according to the invention are safe and may serve as an effective adjunctive therapy to ameliorate multiple side effects of chemotherapy and to enhance the immune system in cancer patients.

Example 2

This study aimed at assessing the efficacy, tolerability and side effects of the formulation of the invention as a complement to neoadjuvant and adjuvant chemotherapy treatment of breast cancer patients. The study shed light on the clinical importance and implications of the unique formulation of the invention described herein, as adjunctive treatment for ameliorating multiple side effects of chemotherapy in breast cancer treatment.

Study methodology: The clinical study is a unicenter, randomized, double-blind placebo controlled clinical trial.

Population: Breast cancer patients receiving neoadjuvant and adjuvant treatment of Tel Aviv Medical Center Oncology Department.

Patients were treated for a minimum of 20 weeks, starting 2 weeks prior to chemotherapy, clinically evaluated every 6 weeks, up to 1 month post chemotherapy.

The follow-up was according to the usual protocol in neoadjuvant and adjuvant chemotherapy.

Imaging methods: Patients entering the trial were evaluated by imaging methods according to conventional protocol, as other patients treated with neoadjuvant and adjuvant chemotherapy. Patients receiving neoadjuvant chemotherapy in the trial had core biopsy histologically proven breast cancer. Clinical or sonographic suspicious auxiliary lymph nodes were further evaluated by FNA or core biopsy. For patients receiving neoadjuvant chemotherapy, metallic markers were introduced with ultrasonographic guidance, during the chemotherapeutic treatment. Post surgery patients were evaluated only by their pathological results from the tumor removed. The following methodologies were employed in the course of evaluation:

1. Mammography: Standard two views examinations of both breasts complemented by 90° lateral view and magnifications views.
2. Whole breast ultrasound with evaluation of the axillas.
3. Breast MRI of both breasts or PET-CT. Potentially more accurate of both previous methods in evaluation of the disease extension and in the evaluation of the contralateral breast for occult disease by other methods.

Chemotherapy: Neoadjuvant, adjuvant and treatment standard chemotherapeutic protocols for breast cancer.

Chemotherapy was administered according to standard adjuvant or neoadjuvant protocols for breast cancer treatment. Most of the patients received a combination of doxorubicin (Adriamycin), cyclophosphamide (Cytophosphan) and paclitaxel (Taxol) (AC+T) or doxorubicin (Adriamycin), cyclophosphamide (Cytophosphan) and 5-fluorouracil (5FU) (CAF), according to accepted international chemotherapy protocols.

Herbal treatment: Formulation 1 of the invention. Each of the herbal components was in the form of an encapsulated dried herbal extract powder imported by the "ZEN" Herb Company and manufactured under GMP conditions.

Patients were divided into two groups:

Group A: received formulation 1 in a dosage of 6 grams (2×3 grams) per day.

Group B: received placebo, resembling the herbal capsules in taste, texture and appearance, and consisting of flavored bred crams.

Visit 1: 2 weeks prior to chemotherapy—

Patients meeting inclusion criteria received an information sheet, signed informed consent form and then evaluated by an oncologist and given the herbal formula. Next, patients were randomly divided into the 2 groups A and B, as above (a formulation group and a placebo group).

Randomization was made in a manner that each group consisted of a similar number of patients of each malignancy.

Visits 2-8: every 3 weeks (according to neo-adjuvant or adjuvant chemotherapy standard protocol)—

Visits included oncologist evaluation and physical examination according to standard protocol.

Patients in the research were handled in a double blind-fashion. Each patient received a sealed container with a 21-day supply of pills, containing 315 pills: calculated as 5 pills 3 times a day for 21 days. During each follow up visit the patients received the next dosage. Instructions were to take the 5 capsules 30 min before meals, 3 times a day.

Treatment was started 2 weeks prior to the first dose of chemotherapy and lasted to the last day of chemotherapy. Patients were seen by attending physicians at least every 6 weeks and had blood counts before each chemotherapy dose or when admitted for complication.

Table 11 summarizes the demographic data for the study group which consisted of 65 breast cancer female patients with localized tumors. Thirty-four were randomized to receive formulation 1 and thirty-one to receive placebo. The median age was 52 years (range 24-68), about a third of the patients were treated in the neoadjuvant setting while the rest received adjuvant therapy. The use of dose-dense and taxane-based regimens was equally distributed among the study groups. Two patients in each group did not start the allocated protocol. Full compliance with treatment arm was assigned to 24 of 34 women allocated to formulation 1 and to 17 of those assigned to placebo.

TABLE 11

Clinical and demographic characteristics at baseline.

|  | Formulation 1 | Placebo | P-value |
|---|---|---|---|
| No of patients | 34 | 31 | |
| Age | | | |
| median | 47.58 | 52.16 | |
| range | 24-67 | 28-68 | |
| Histology | | | 0.32 |
| Invasive Ductal (IDC) | 20 | 24 | |
| Invasive Locular (ILC) | 2 | 2 | |
| IDC + ILC | 11 | 5 | |
| Other | 1 | | |
| Hormone receptors: | | | |
| ER, PR | | | |
| Negative | 8 | 5 | 0.46 |
| positive | 26 | 26 | |
| Her-2 | | | |
| Negative | 26 | 19 | 0.11 |
| Intermediate | 5 | 3 | |
| Positive 3 | 3 | 9 | |
| Protocol Compliance | | | 0.39 |
| Full compliance | 24 | 17 | |
| Partial compliance | 8 | 12 | |
| Not started | 2 | 2 | |

Hematological toxicities associated with anemia (hemoglobin concentration of less than 10 gram %) and neutropenia and leucopenia (total WBC<$3.0 \times 10^9$/L or absolute neutrophile (ANC) count <$1000 \times 10^9$/L) were significantly reduced in patients treated with the formulation of the invention (Table 12). In sub-group analysis according to chemotherapy schedules, the protective effect against anemia was noticed only in groups receiving Adriamycin and Cytoxan every 3 weeks (hemoglobin concentration of less than 10 gram in 4% of patients treated with the formulation of the invention and 50% of placebo patients, p=0.003), while the protective effect against neutropenia was noticed only in the dose-dense group (ANC<$1.5 \times 10^9$/L in 33% of placebo patients and 0% of groups treated with the formulation of the invention, respectively). Neutropenic fever episodes occurred in 2 and 4 patients of the formulation-treated and placebo groups, respectively, non-significant difference (p=0.32). Sever infections occurred in 3 patients in the placebo group and none in the group treated with the formulation, non-significant difference (p=0.10)).

TABLE 12

Hematological Toxicity by treatment group

| | Grade 1 and under (%) | Above grade 1 (Grade 2-4) (%) | P value |
|---|---|---|---|
| Anemia | <10.0 g/dl | >10.0 g/dl | |
| CHM | >28(82%) | 6(18%) | 0.0081 |
| Placebo | 16(52) | 15(48) | |
| Leukopenia | <$3.0 \times 10^9$/L | >3.0 | |
| CHM | 28(82) | 6(18) | 0.0315 |
| Placebo | 18(58) | 13(42) | |
| neutropenia | <$1.5 \times 10^9$/L | >1.5 | |
| CHM | 25(73) | 9(27) | 0.063 |
| Placebo | 16(52) | 15(48) | |
| Thrombocytopenia | <$75.0 \times 10^9$/L | >75.0 | |
| CHM | 34(100) | 0 | 0.258 |
| Placebo | 28(3) | 2(7) | |
| Lymphopenia | <0.8 | >0.8 | |
| CHM | 23(68) | 11(32) | 0.2139 |
| Placebo | 16(51) | 15(49) | |
| | Grade 2 and under (%) | Above Grade 2 (%) | P value |
| Leukopenia | <$2.0 \times 10^9$/L | >2.0 | |
| CHM | 33(97) | 1(3) | 0.0475 |
| Placebo | 18(58) | 13(42) | |
| neutropenia | <$1.0 \times 10^9$/L | >1.0 | |
| CHM | 30(88) | 4(12) | 0.0447 |
| Placebo | 21 (52) | 10(32) | |
| Lymphopenia | <$0.5 \times 10^9$/L | >0.5 | |
| CHM | 31(91) | 3(9) | 1.0 |
| Placebo | 28(90) | 3(10) | |

Example 3

Cell Culture and Reagents

The human Breast cell lines, MDA-231 and MDA-453, were obtained from the American Type Culture Collection (ATCC). Both cell lines were grown and maintained in Dulbecco's modified Eagle's medium (DMEM, Biological Industries, Beit HaEmek, Israel) supplemented with 10% fetal calf serum (FCS), 1% penicillin and 1% streptomycin (full medium) at 37° C., in an atmosphere of 95% oxygen and 5% $CO_2$.

The herb formulation is the formulation of the invention as described herein.

Cell Viability Assay:

Cells ($2-5 \times 10^3$/well) were seeded in 96-well plastic plates and incubated at 37° C. in full medium containing the tested formulation. After 48 and 72 hours, cell viability was assessed by the ability of metabolically active cells to reduce tetrazolium salt (XTT) to colored formazan compounds. The absorbance of the samples was measured with an ELISA reader (wavelength 450 nm, reference wavelength 630 nm). Each measurement was performed in triplicate. The data are mean values from three different experiments.

The treatment was started after 24 h of cell culturing in order to determine the effect of the formulation of the invention on cell survival. This effect was calculated by comparing the density of the intact cells to the density of the treated cells. Cell density was determined by the XTT assay as follows. Cells ($2-5 \times 10^3$/well) were seeded in 96-well plastic plates and incubated at 37° C. in full medium containing the test drugs. The formulation of the invention was added in varying concentrations (1-100 mg/ml) to each of three replicate wells and incubated for 72 h. A freshly prepared mixture of XTT and an activation reagent (PMS) was added to each well (50 μl). Following 2 h of incubation at 37° C., the plates were placed on a mechanical plate shaker of a computerized automatic micro-well plate spectrophotometer and shaken for 30 sec and the optical densities (ODs) of the dye were read at 450 nm. The measurements were repeated following 4 and 6 h of incubation. The time point of the assay at which there were optimal OD readings was chosen to count the cell number. When more than one time point fitted this criterion, the results for the different time points were normalized and averaged. The OD readings were previously shown to correlate well (r>0.97-0.99) with the number of cells/well.

Light Microscopy.

T47D breast adenocarcinoma cells were plated at a density of $5 \times 10^6$ per 10-cm dish with different concentrations of the herbal formulation of the invention and after 24 h visualized by light microscopy ×200.

Flow Cytometry Analysis.

T47D cells were plated at a density of $5 \times 10^6$ per 10-cm dish with the test drugs at selected concentrations. The adherent and non-adherent cells were collected during exponential growth of the cells and counted. A total of $1-2 \times 10^6$ cells were washed in phosphate-buffered saline (PBS) and the pellet was fixed in 3 ml ethanol for 1 h at 4° C. Before the analysis, the cells were pelleted and resuspended in 1 ml PBS and incubated for 30 min with 0.64 mg/ml RNAse at 37° C. They were stained with 45 propidium iodide (PI) for at least 1 h before analysis by flow cytometry. Data acquisition was performed on a FACScan and analyzed by CellQuest software (Becton Dickinson Immunocytometry Systems, San Jose, Calif., USA). All fluorescence and laser light scatter measurements were made with linear signal processing electronics. Data for at least 15,000 cells were collected for each data file. A standard protocol for cell cycle distribution and cell size was used. Necrotic cells were excluded by counting cells following staining with trypan blue before fixation. All experiments were done three times.

Statistical Analysis.

The results were calculated as mean±SE. The difference between the intact and treated cells was evaluated by the one-way Student's T-test using an SPSS software package (SPSS Inc., Chicago, Ill., USA). Significance (p<0.05) was established by the post hoc Tukey's pairwise comparison.

Effect of the Formulation of the Invention on Cell Survival.

Figure 4:
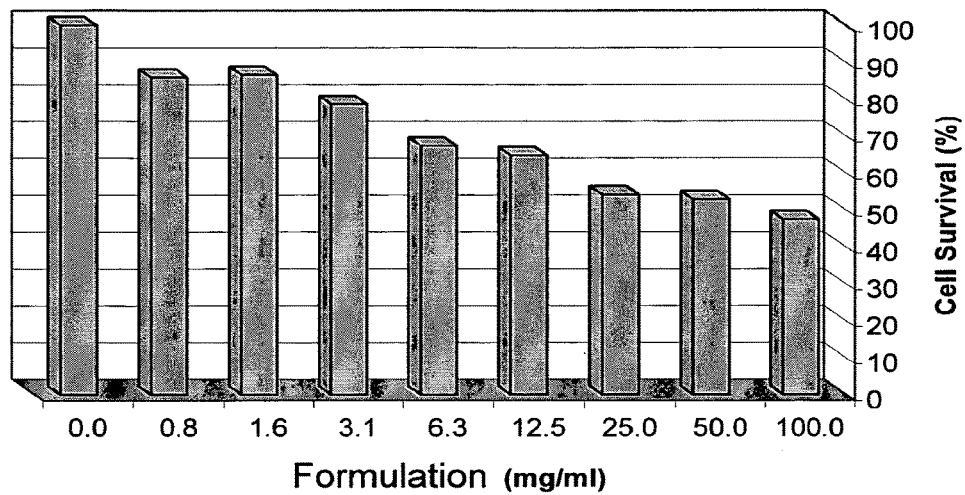
FIG. 4 is a bar representation demonstrating the effect of a formulation of the invention on MDA-231 cells survival.
Figure 5:
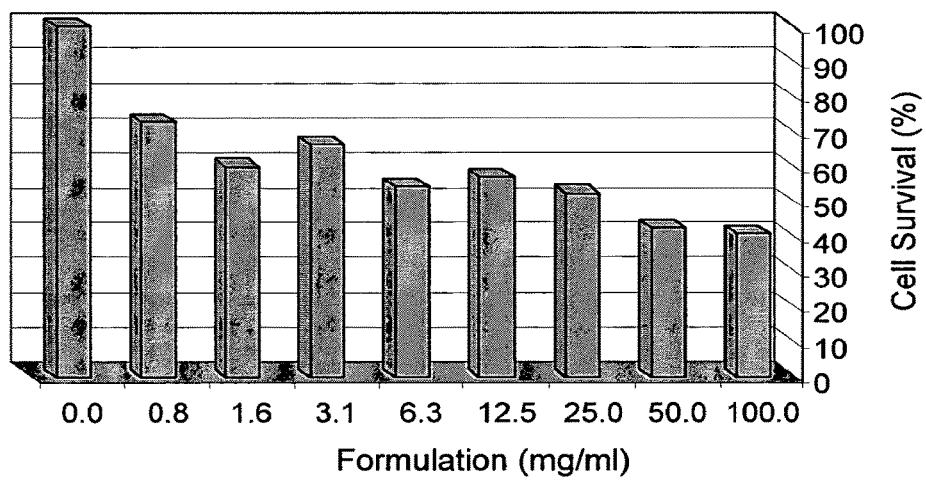
FIG. 5 is a bar representation demonstrating the effect of a formulation of the invention on MDA-453 cells survival.
Figure 6:
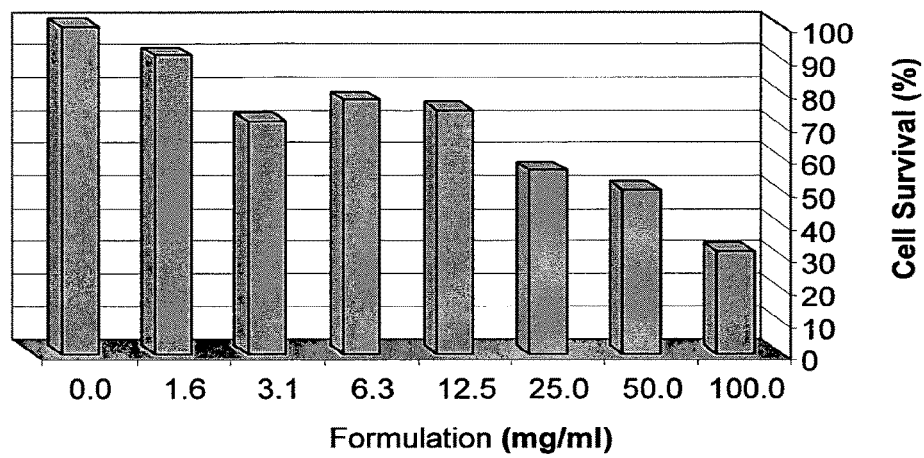
FIG. 6 is a bar representation demonstrating the effect of a formulation of the invention on T47D cells survival.

A dose-dependent inhibitory effect of the formulation of the invention on cells survival was found in MDA-231, MDA-453 and T47D human breast carcinoma cell lines (FIGS. 4, 5 and 6, respectively). IC50 was approximately similar (25 mg/ml) on all 3 carcinoma cell lines tested.

Figures 7A, 7B, 7C:
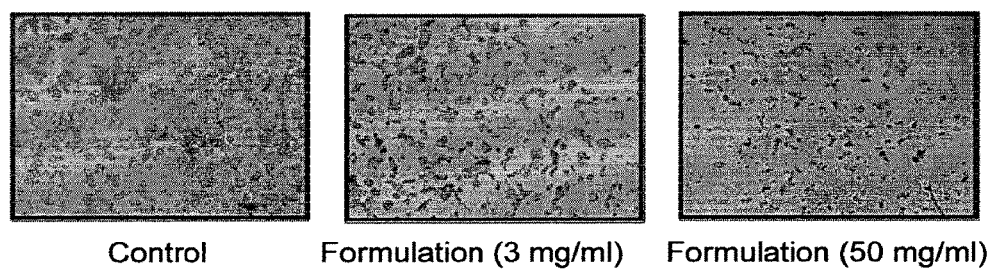
FIGS. 7A-C are light microscopy images depicting the effect of the formulation of the invention on breast cancer adenocarcinoma cell line (T47D).

Assays were also conducted with breast cancer adenocarcinoma cells (T47D). The results are presented in FIGS. 7A-C. As demonstrated, administration of the formula of the invention causes cell death of cancer cells and does not only reduce side effects associated with the treatment, thereby making chemotherapy treatments more effective and also having additional effect in reducing the recurrence of the treated disease.

Induction of Apoptosis.

Figure 8A:
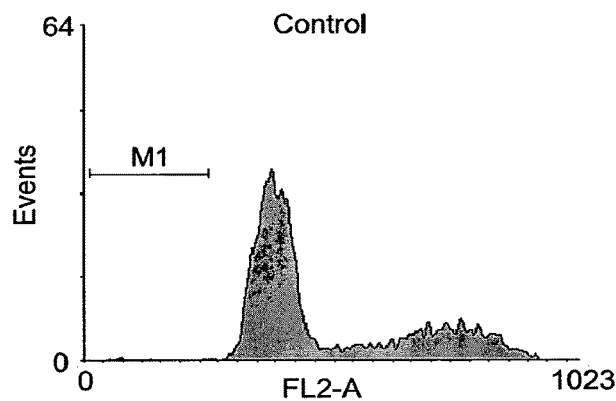
FIGS. 8A-C are flow cytometry analysis of apoptosis of T47D carcinoma cell line.
Figure 8B:
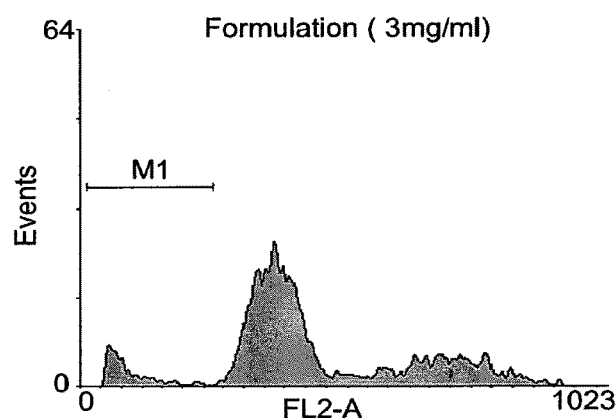
Figure 8C:
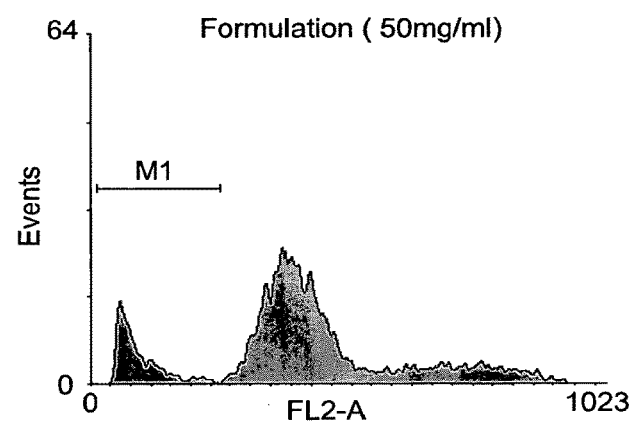

The extent of apoptosis was assessed by flow cytometry analysis following 72 h of exposure of the cells to the different concentrations of the formulation of the invention. The formulation of the invention increased the percentage of cells with sub-diploid DNA content, the hallmark of apoptosis, in a dose-dependent manner in the T47D carcinoma cell line (FIGS. 8A-C).

The invention claimed is:

1. A method for reducing recurrence of bladder cancer, the method comprising administering to a subject in need thereof a herbal formulation comprising Poriae Cocos, Radix Paeoniae Lactiflorae, Ligustrum Lucidum, Ophiopogon Japonicus, Scutellaria Barbata, Taraxaci Mongolici Cum Radice Herba and Prunella Vulgaris.

2. A method for reducing recurrence of bladder cancer, the method comprising administering to a subject in need thereof a herbal formulation comprising Astragalus Membranaceus, Poriae Cocos, Radix Paeoniae Lactiflorae, Ligustrum Lucidum, Ophiopogon Japonicus, Oldenlandia Diffusa, Scutellaria Barbata, Taraxaci Mongolici Cum Radice Herba and Prunella Vulgaris.

3. The method according to claim 2, wherein the formulation further comprising at least one of Glehnia Littoralis, Citrus Reticulata, Radix Et Caulis Jixueteng, Atractylodes Macrocephala, Paeonia Obovata and Lycium Chinense.

\* \* \* \* \*